(12) United States Patent
Esenaliev et al.

(10) Patent No.: US 11,730,979 B2
(45) Date of Patent: Aug. 22, 2023

(54) NANOPULSE LIGHT THERAPY

(71) Applicant: Board of Regents, The University of Texas System, Austin, TX (US)

(72) Inventors: Rinat O. Esenaliev, League City, TX (US); Maria-Adelaide Micci, Dickinson, TX (US); Donald S. Prough, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/339,032

(22) PCT Filed: Oct. 5, 2017

(86) PCT No.: PCT/US2017/055423
§ 371 (c)(1),
(2) Date: Apr. 3, 2019

(87) PCT Pub. No.: WO2018/067876
PCT Pub. Date: Apr. 12, 2018

(65) Prior Publication Data
US 2019/0224500 A1    Jul. 25, 2019

Related U.S. Application Data

(60) Provisional application No. 62/404,649, filed on Oct. 5, 2016.

(51) Int. Cl.
*A61N 7/00*     (2006.01)
*A61B 18/26*    (2006.01)

(52) U.S. Cl.
CPC ............... *A61N 7/00* (2013.01); *A61B 18/26* (2013.01); *A61B 2018/266* (2013.01); *A61N 2007/0026* (2013.01)

(58) Field of Classification Search
CPC .. A61N 7/00; A61N 2007/0026; A61B 18/26; A61B 2018/266
See application file for complete search history.

(56) References Cited

U.S. PATENT DOCUMENTS 5,041,121 A * 8/1991 Wondrazek ............ A61B 18/26
606/15
6,022,309 A    2/2000 Celliers et al.
(Continued)

OTHER PUBLICATIONS

International Search Report issued in counterpart International Application PCT/US2017/055423, dated Apr. 13, 2018.

*Primary Examiner* — Lynsey C Eiseman
*Assistant Examiner* — Jessandra F Hough
(74) *Attorney, Agent, or Firm* — Thomas Horstemeyer, LLP

(57) ABSTRACT

Provided herein are noninvasive stimulation methods and apparatus for the treatment of injury to tissues using a novel pulsed laser system that combines the benefits of near-infrared laser light and optoacoustic waves. In certain embodiments, short, high-energy laser light pulses generate low intensity ultrasound waves that travel deep into brain tissues to stimulate neural function and treat neurological dysfunctions. In certain embodiments, a patient interface is provided wherein optoacoustic waves are produced by a plurality of optical absorbers overlying all of a plurality of optical fibers while in other embodiments optoacoustic waves are generated both inside the tissue and outside the tissue via a plurality of optical absorbers overlying some but not all of the optical fibers thus enabling an option of varying proportions of optoacoustic waves generated inside and outside of tissue.

8 Claims, 12 Drawing Sheets

(56) References Cited

U.S. PATENT DOCUMENTS

| | | | |
|---|---|---|---|
| 6,428,532 B1* | 8/2002 | Doukas | A61B 18/20 |
| | | | 359/245 |
| 6,498,942 B1* | 12/2002 | Esenaliev | A61B 5/0095 |
| | | | 600/310 |
| 6,501,591 B1* | 12/2002 | Kumar | G02F 1/395 |
| | | | 359/326 |
| 7,534,255 B1 | 5/2009 | Streeter et al. | |
| 8,523,926 B2 | 9/2013 | Neev | |
| 8,858,607 B1* | 10/2014 | Jones | A61N 5/0616 |
| | | | 607/88 |
| 2005/0131289 A1* | 6/2005 | Aharoni | A61B 8/12 |
| | | | 600/407 |
| 2005/0137656 A1 | 6/2005 | Malak | |
| 2006/0004306 A1* | 1/2006 | Altshuler | A61H 39/002 |
| | | | 601/3 |
| 2008/0045865 A1* | 2/2008 | Kislev | A61B 5/411 |
| | | | 601/3 |
| 2011/0188251 A1* | 8/2011 | Kalms | B23K 26/0652 |
| | | | 362/259 |
| 2014/0205965 A1* | 7/2014 | Boutoussov | A61C 17/02 |
| | | | 433/29 |
| 2014/0276247 A1 | 9/2014 | Hall et al. | |
| 2015/0283277 A1 | 10/2015 | Schafer et al. | |
| 2016/0220821 A1* | 8/2016 | O'Connell | A61N 1/36064 |

\* cited by examiner

NSC were treated for 5 minutes with:

L = light (808nm)

L + U = nanopulsed light (808 nm) + ultrasound

U = ultrasound induced by nanopulsed light (808 nm)

TBI

TBI + NPLT

TBI

TBI + NPLT

NANOPULSE LIGHT THERAPY

REFERENCE TO RELATED APPLICATIONS

This application claims priority based on PCT/US2017/055423, filed Oct. 5, 2017, which in turn claims priority based on U.S. Provisional Application Ser. No. 62/404,649, filed Oct. 05, 2016, each of which are incorporated herein by reference in their entireties.

FIELD OF THE INVENTION

This invention relates generally to methods and apparatus for treatment of tissue injury using light pulses.

BACKGROUND OF THE INVENTION

Without limiting the scope of the invention, its background is described in connection with existing treatment for traumatic tissue injury including traumatic brain injury. Non-invasive therapies are also lacking for treatment of stroke, age-related (presenile) dementia, neurodegenerative diseases, cognitive decline in the elderly as a consequence of atherosclerosis, and in treatment of patients experiencing cognitive decline caused by normal pressure hydrocephalus.

Each year, there are about 1.5 million new cases of traumatic brain injury (TBI) in the United States. Of these patients, approximately 230,000 require hospitalization, over 80,000 to 90,000 are disabled, and 50,000 die. Head injury causes nearly 50 billion dollars in medical expenses and lost productivity annually, making TBI one of the major health care problems in the United States. There are more than 5.3 million and 7.7 million people living with disabilities from TBI in the United States and European Union, respectively. Thus, while there are approximately 250,000 new hospitalizations for TBI in the U.S. annually, there are millions of TBI survivors in the U.S. and worldwide. Unfortunately, some of these survivors suffer from the consequences of TBI their entire lives. There is currently no cure for TBI.

Over the past two decades, blast-induced neurotrauma (BINT) has become a prevalent health concern due to the increasing incidence of blast-induced TBI sustained by soldiers in combat. Many victims of closed-head, blast injury experience persistent post-concussive symptoms and chronic cognitive and emotional deficits secondary to the initial TBI. Although the understanding of TBI pathophysiology has improved, current treatment options for BINT remain limited.

Provided herein is the discovery of an innovative, efficient therapy of TBI as well as other diseases and conditions. The disclosed therapeutic approaches are applicable to therapy of many diseases and conditions including, but not limited to TBI.

BRIEF SUMMARY OF THE INVENTION

Provided herein are methods and apparatus for combined light and optoacoustic therapy of tissue injury. In general, light pulses in a spectral range from 400 nm to 2000 nm can be employed for this therapy.

In some embodiments, near-infrared light pulses in a spectral range from 680 to 1400 nm are provided together with simultaneous delivery of optoacoustic (ultrasound) waves at a frequency of 0.01-100 MHz. In certain embodiments, near-infrared light pulses in a spectral range from 680 to 950 nm are provided together with simultaneous delivery of optoacoustic (ultrasound) waves at a frequency of 0.01-100 MHz.

Many types of pulsed light sources can be used for this therapy including, but limited to solid-state lasers, optical parametric oscillators (OPOs), semiconductor lasers (e.g. diode lasers), liquid lasers, dye lasers, gas lasers, light-emitting diodes (LEDs), as well as non-laser optical sources.

In certain embodiments both the light and optoacoustic therapies are provided by a single instrument that delivers short pulses of high intensity near-infrared laser light in a spectral range from 680 to 950 nm that generate ultrasonic (optoacoustic) waves by each short laser pulse within the tissue.

In certain embodiments the optical pulses are provided with a pulse duration equal to or shorter than approximately 1 microsecond depending on tissue type and light wavelength. In certain embodiments, the pulse duration is in the range from about 1 femtosecond to about 1 microsecond. In still further embodiments, the pulse duration is in a range from about 1 femtosecond to about 10 nanoseconds. In still other embodiments, the pulse duration is in a range from about 1 nanosecond to about 10 nanoseconds.

In one embodiment, a system is provided for the delivery of pulsed near-infrared light with energy levels and pulse durations that produce wide-band low-energy optoacoustic (ultrasound) waves in the tissue via a thermoelastic mechanism under stress-confined irradiation conditions. Also provided is a system for delivery of pulsed light for treatment of traumatic or disease related injury comprising a patient interface adapted to be placed against a skin of a patient over a tissue to be treated, wherein the pulsed light is provided through the patient interface with a pulse duration ranging from 1 femtosecond to 1 microsecond and in a spectral range from 400 to 2000 nm, and the pulsed light delivered through the patient interface produces wide-band low-energy ultrasound waves in the tissue via a thermoelastic mechanism under stress-confined irradiation conditions. In certain embodiments the system provides pulsed light at an energy of up to 15 mJ. In certain embodiments, the pulsed light is communicated to through the patient interface via fiber optics. The fiber optics are in optical communication via a fiber optic connector with a tunable optical parametric oscillator that generates the pulsed light in certain embodiments. Alternatively, the pulsed light may be generated by light emitting diodes mounted on the patent interface.

In certain embodiments the system generates near-infrared laser light pulses in a spectral range from 680 to 950 nm, at a pulse duration of about 1 to about 10 nanoseconds and a repetition rate of 0.1 Hz to 1 MHz. In other embodiments, the system provides nanosecond pulsed near-infrared laser light at about 800-850 nm at pulse duration of about 5-10 nanoseconds. In one exemplified embodiment, pulsed near-infrared light at about 808 nm is provided at pulse duration of about 5-10 ns, energy of up to 15 mJ, and pulse repetition rate of about 20 Hz to produce low-level, wide-band, MHz optoacoustic (ultrasound) waves that travel deep into the brain.

In certain embodiments, a patient interface is provided that includes a plurality of separate pulsed light outlets. In one embodiment, at least one of the separate pulsed light outlets is overlayed with an optical absorber that generates optoacoustic waves outside of the tissue.

In one embodiment, the ultrasound inducing light pulses are used in treatment of traumatic brain injury, stroke, age-related (presenile) dementia, neurodegenerative diseases, cognitive decline in the elderly as a consequence of atherosclerosis, and in treatment of patients experiencing cognitive decline caused by normal pressure hydrocephalus.

In certain embodiments, higher optoacoustic wave doses are provided through use optical absorbers on skin surfaces over tissues to be treated in order to generate optoacoustic waves at higher amplitudes than those generated naturally within tissues by the light pulses. The absorbers include, but are not limited to liquid, solid state (metal, ceramics, semiconductors, plastics, glass) and gas state absorbers. Liquid absorbers may include alcohol or water-containing liquids including strongly absorbing chromophores.

The methods and apparatus disclosed herein will significantly and rapidly improve therapy and management because it is based on a noninvasive laser system that provides light pulses with therapeutic doses and without any damage to tissues.

BRIEF DESCRIPTION OF THE DRAWINGS

For a more complete understanding of the present invention, including features and advantages, reference is now made to the detailed description of the invention along with the accompanying figures:

FIG. 4B represents BDNF mRNA expression. FIG. 4C represents Stat3 mRNA expression. FIG. 4D represents CASP3 mRNA expression. FIG. 4E represents BAX mRNA expression. FIG. 4F represents Bcl-2 mRNA expression.

FIG. 8A shows the expression of miR9. FIG. 8B shows the expression of miR29. FIG. 8C shows the expression of miR25.

FIG. 10A represents coronal sections stained with anti-CD68 in TBI rats. FIG. 10B represents coronal sections stained with anti-CD68 in TBI +NPLT treated rats. FIG. 10C represents coronal sections stained with anti-Iba1 in TBI rats. FIG. 10D represents coronal sections stained with anti-Iba1 in TBI+NPLT treated rats.

DETAILED DESCRIPTION

Figure 1A:
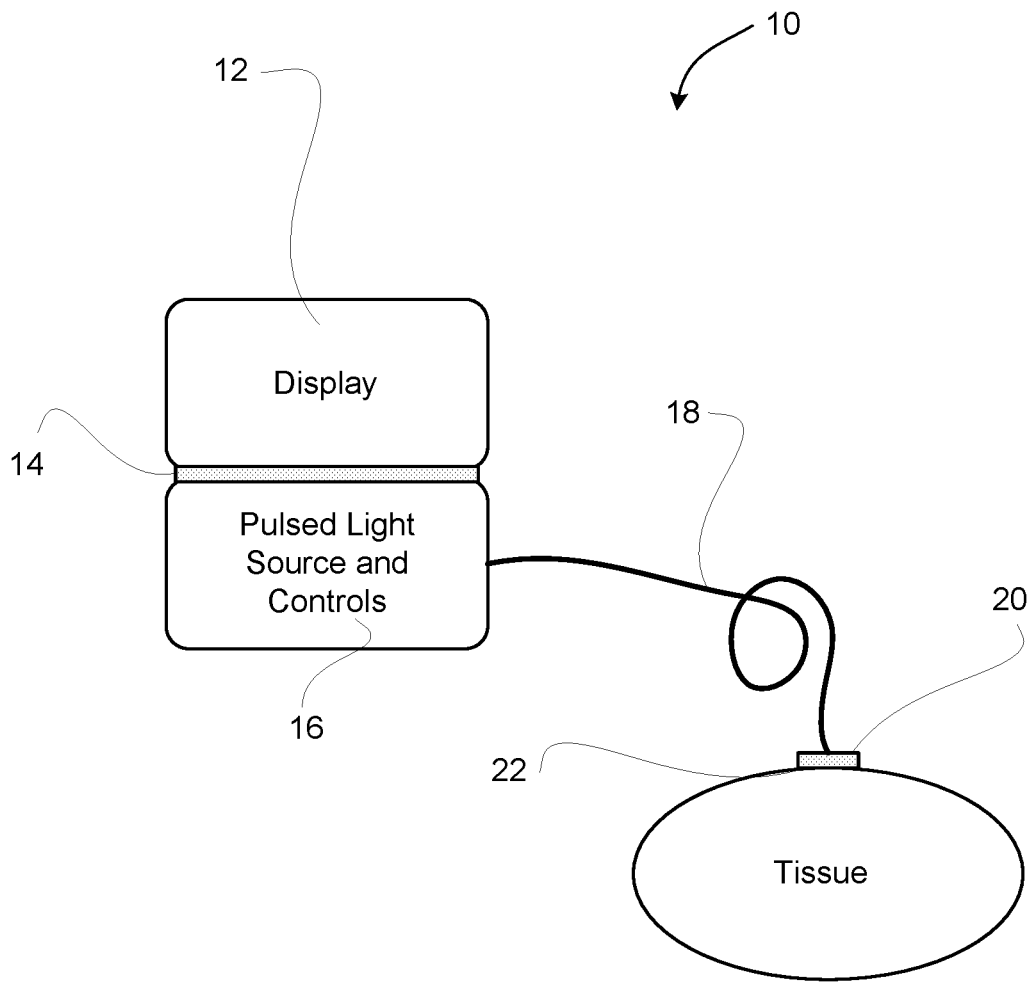
FIG. 1A represents one embodiment of a delivery platform for a noninvasive, medical-grade laser system that provides short (nanosecond) pulses in the near infrared spectral range for Nano-Pulsed Light Therapy (NPLT) according to one embodiment of the present invention.

Provided herein are noninvasive stimulation methods and apparatus for the treatment of injured tissue including brain injury using Nano-Pulsed Light Therapy (NPLT). In one embodiment a system is provided that generates short, high-energy laser light pulses together with low intensity ultrasound waves that travel deeper into the brain to stimulate neural function and treat neurological dysfunctions. In a particular embodiment described herein, a novel, noninvasive NPLT system is provided that combines the benefits of near-infrared light (808 nm) and of ultrasound (optoacoustic) waves, which are generated with each short laser pulse within the tissue.

ABBREVIATIONS: The following abbreviations are used throughout this application:
BAX Bcl-2 associated X protein , regulator of apoptosis
Bcl-2 B-Cell Lymphoma 2 is a regulator protein that regulated cell death
BDNF Brain Derived Neurotropic Factor
BINT Blast-Induced Neurotrauma
CD68 Cluster of Differentiation 68, serves as a marker of activated microglia in the brain
GAPDH Glyceraldehyde 3-phosphate dehydrogenase, constitutively expressed housekeeping gene
LLLT Low Level Laser Therapy
NPLT Nano-Pulsed Light Therapy
NLPDT Nano-Pulsed Light Diagnostics and Therapy
NSC Neural Stem Cells
PID Post-Injury Days
STAT3 Signal Transducer and Activator of Transcription 3
TBI Traumatic Brain Injury To facilitate the understanding of this invention, and for the avoidance of doubt in construing the claims herein, a number of terms are defined below. Terms defined herein have meanings as commonly understood by a person of ordinary skill in the areas relevant to the present invention. The terminology used to describe specific embodiments of the invention does not delimit the invention, except as outlined in the claims.

The terms such as "a," "an," and "the" are not intended to refer to a singular entity unless explicitly so defined, but include the general class of which a specific example may be used for illustration. The use of the terms "a" or "an" when used in conjunction with "comprising" in the claims and/or the specification may mean "one" but may also be consistent with "one or more," "at least one," and/or "one or more," "at least one," and/or "one or more than one."

The use of the term "or" in the claims is used to mean "and/or" unless explicitly indicated to refer to alternatives as mutually exclusive. Thus, unless otherwise stated, the term "or" in a group of alternatives means "any one or combination of" the members of the group.

Further, unless explicitly indicated to refer to alternatives as mutually exclusive, the phrase "A, B, and/or C" means embodiments having element A alone, element B alone, element C alone, or any combination of A, B, and C taken together.

Similarly, for the avoidance of doubt and unless otherwise explicitly indicated to refer to alternatives as mutually exclusive, the phrase "at least one of" when combined with a list of items, means a single item from the list or any combination of items in the list. For example, and unless otherwise defined, the phrase "at least one of A, B and C," means "at least one from the group A, B, C, or any combination of A, B and C." Thus, unless otherwise defined, the phrase requires one or more, and not necessarily not all, of the listed items.

The terms "comprising" (and any form thereof such as "comprise" and "comprises"), "having" (and any form thereof such as "have" and "has"), "including" (and any form thereof such as "includes" and "include") or "containing" (and any form thereof such as "contains" and "contain") are inclusive or open-ended and do not exclude additional, unrecited elements or method steps.

The term "effective" as used in the specification and claims, means adequate to provide or accomplish a desired, expected, or intended result. The terms "about" or approximately" are defined as being close to as understood by one of ordinary skill in the art, and in one non-limiting embodiment the terms are defined to be within 10%, within 5%, within 1%, and in certain aspects within 0.5%.

In one embodiment described herein, a novel, non-invasive Nano-Pulsed Light Therapy (NPLT) system is provided that combines the benefits of near-infrared light (808 nm) and of ultrasound (optoacoustic) waves, which are generated with each short laser pulse within the tissue. Confirmation of the unique effectiveness of the NPLT was obtained in a rat model of blast-induced neurotrauma where it was determined that transcranial application of NPLT provides significant neuroprotective effects.

In one embodiment tested herein, light was provided by laser pulses that were applied on the intact rat head 1 hour after injury using a specially developed fiber-optic system. Vestibulomotor function was assessed on post-injury days (PID) 1-3 on the beam balance and beam walking tasks. Cognitive function was assessed on PID 6-10 using a working memory Morris Water Maze test. BDNF and caspase-3 mRNA expressions were measured by qRT-PCR in laser-captured cortical neurons. Microglia activation and neuronal injury were assessed in brain sections by immunofluorescence using specific antibodies against CD68 and active caspase-3, respectively.

In the vestibulomotor and cognitive tests, NPLT-treated animals performed significantly better than a blast-induced neurotrauma (BINT) group and performed similarly to SHAM animals. NPLT up-regulated mRNA encoding BDNF and down-regulated the pro-apoptotic protein caspase-3 in cortical neurons. Immunofluorescence demonstrated that NPLT inhibited microglia activation and reduced the number of cortical neurons expressing activated caspase-3. NPLT also increased expression of BDNF in the hippocampus and the number of proliferating progenitor cells in the dentate gyms. The data demonstrate a neuroprotective effect of NPLT that far exceeds the prior results obtained with transcranial low level laser therapy (LLLT) or ultrasound.

Transcranial low level laser therapy (LLLT) has gained greater interest as an alternative to existing TBI treatments. LLLT uses near-infrared light (600 nm to 1000 nm) to stimulate, repair, regenerate, and protect injured tissue. Initial studies of LLLT were focused on stimulation of wound healing and reduction of pain and inflammation in various orthopedic conditions. Recently, several reports demonstrated beneficial effects of LLLT in reducing neuroinflammation, brain lesion volume, and edema in animal models of TBI. Specifically, they showed a significant neuroprotective effect of transcranial LLLT generated by LED or laser sources (continuous or long pulsed) using controlled cortical impact and closed head injury rodent models of TBI. The long pulsed light used in those studies (pulse duration of tens of milliseconds) cannot generate optoacoustic (ultrasonic) waves because long pulses cannot provide the condition of stress confinement that is necessary for generating optoacoustic (ultrasonic) waves. More recently, some clinical case reports tested the therapeutic effect of LLLT for the treatment of chronic TBI patients and showed small but significant improvements in cognitive and motor functions, however, as of the present, no studies have tested LLLT on animal models of blast-induced neurotrauma (BINT).

In the past few years, new evidence emerged pointing at a potential therapeutic use of non-invasive low-intensity, low-frequency (0.44-0.67 MHz) ultrasound waves for treatment of TBI. Specifically, recent studies have shown that transcranial delivery of low-intensity pulsed ultrasound stimulation reduces brain injury caused by focused ultrasound-induced blood brain barrier permeability and reduces edema in a closed head weight drop model of TBI.

However, the present invention provides a unique application of optoacoustics to combine the therapeutic effects of light and ultrasound. Optoacoustic waves can be generated in tissues by short (typically, hundreds of nanoseconds or shorter) optical pulses. Absorption of light energy in tissue or any other absorbing medium is followed by temperature rise. Thermal expansion of the irradiated medium induces mechanical stress (pressure rise) upon the condition of stress confinement. This mechanism is referred to as the thermoelastic mechanism of pressure generation. The condition of stress confinement means that there is insignificant stress relaxation in the irradiated volume during the optical pulse. To provide this condition in tissues, the duration of the optical pulse should be shorter than the time of stress propagation out of the irradiated tissues volume.

In certain embodiments provided herein, nanosecond laser pulses are used to generate conditions of stress confinement for the presently disclosed NPLT. It should be noted that optoacoustic waves have a wide frequency range (from approximately 0.01 MHz to approximately 100 MHz, or even wider depending on wavelength, pulse duration, and tissue properties), while the ultrasound waves used in the ultrasound therapy studies have only one frequency or a narrow frequency range.

In certain embodiments provided herein, light plus ultrasound combinations provide more efficient therapy than light or ultrasound alone. Moreover, a surprisingly synergistic effect was shown to be produced when light pulses and light-induced ultrasound (optoacoustic) waves were applied simultaneously resulting in a better therapeutic response.

In certain embodiments, a novel, medical grade optoacoustic system is provided for the transcranial delivery of near-infrared light pulses (808 nm) and low low-level optoacoustic (ultrasound) waves. This system generates pulses with a duration of 10 ns, energy of up to 15 mJ, and pulse repetition rate of 20 Hz. It can produce wide-band, low-energy optoacoustic (ultrasound) waves in the tissue via the thermoelastic mechanism under stress-confined irradiation conditions. Thus, the system has significant therapeutic potential for the treatment of brain injuries because it combines the beneficial effects of both near-infrared light and low-level optoacoustic (ultrasound) waves.

In one embodiment provided herein NPLT is applied transcranially to rats subjected to TBI using two well-established rodent models: Blast-Induced Neurotrauma (BINT; a model of diffuse brain injury) and fluid percussion injury (TBI; a model of blunt head trauma). As shown herein, transcranial application of NPLT significantly reduces neuronal cell death and neuroinflammation, increases neurotrophin expression and proliferation of neural progenitors in the hippocampus, and provides significant vestibulomotor and cognitive improvements.

It should be noted that not only nanosecond pulses can be used for this therapy, in other embodiments short pulses with duration shorter than approximately 1 microsecond are applied. Therefore, the NPLT can be performed using at least one short pulse with a duration from about 1 femtosecond to about 1 microsecond.

Absorption of light energy in a medium is followed by rapid thermal relaxation and a temperature increase in the medium. Thermal expansion of the irradiated medium induces mechanical stress (i.e., pressure rise). In one embodiment a phenomena can be described wherein a short optical pulse with the incident fluence, $F_o$, induces a pressure rise, $P(z)$, in the medium upon condition of stress confinement according to Eq. 1:

$$P(z) = (\beta c_s^2/C_p)\mu_a F = \Gamma \mu_a F(z) = \Gamma \mu_a F_o \exp(-\mu_a z) \quad \text{(Eq. 1)}$$

where $\beta$ [1/° C.] is the thermal expansion coefficient; $c_s$ [cm/s] is the speed of sound; $C_p$ [J/g° C.] is the heat capacity at constant pressure; $F(z)$ [J/cm$^2$] is the fluence of the optical pulse; and $\mu_a$ [cm$^{-1}$] is the absorption coefficient of the medium.

The optoacoustic pressure in Eq. 1 can be expressed in J/cm$^3$ or in bar (1 J/cm$^3$=10 bar). The expression $(\beta c_s^2/C_p)$ in Eq. 1 represents the dimensionless Gruneisen parameter, $\Gamma$. The exponential attenuation of the optical radiation in the medium is represented by $\exp(-\mu_a z)$.

Eq. 1 is valid upon the condition of stress confinement when pressure relaxation is insignificant during the heat deposition. The stress-confined condition is satisfied when light pulse duration, $\tau_p$, is shorter than the stress relaxation time, $\tau_{str}$, in the irradiated volume as follows:

$$\tau_p < \tau_{str}$$

To provide the condition of stress confinement in tissues for efficient optoacoustic pressure generation, the duration of the optical pulses should be shorter than approximately 1 microsecond depending on tissue type and light wavelength. Therefore, the pulse duration should be preferably in the range from about 1 femtosecond to about 1 microsecond.

Unlike LLLT, NPLT utilizes therapeutic effects of both light and optoacoustic (ultrasound) waves. Moreover, the light and ultrasound waves with these parameters may result in synergistic effects that substantially increase efficacy of therapy.

To provide the therapeutic dose and the condition of stress confinement, a novel, medical grade, NPLT system was designed and built for the transcranial delivery of near-infrared light and ultrasound waves to the brain. In one embodiment, the system was operated through custom LabVIEW software running on a medical-grade touch screen PC (an Advantech POC-155 as depicted). The exemplified NPLT system used a tunable optical parametric oscillator that generates nanosecond pulses in the near infra-red spectral range (from 680 to 950 nm) energy of up to 15 mJ, with duration of 7 ns and repetition rate of 20 Hz that produced low-level, wide-band, MHz optoacoustic (ultrasound) waves able to travel deep into the brain.

FIG. 1A represents one embodiment of a delivery platform for a noninvasive, medical-grade laser system that provides short (nanosecond) pulses in the near infrared spectral range for Nano-Pulsed Light Therapy (NPLT) according to one embodiment of the present invention. The system (10) includes a short pulsed light source (16) that has an electrical connection (14) with a display (12) to control the parameters of the system for delivery of NPLT. The light pulses are delivered to a patient using a light delivery system such as a fiber-optic light delivery system which may consist of a fiber-optic connector (18) that might be a bundle or a single fiber. A patient interface (20) is attached to a tissue surface (22) and is used to target light to the underlying treatment site in the patient's tissue.

Figure 1B:
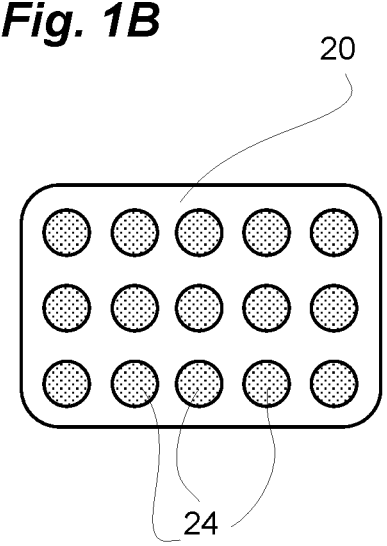
FIG. 1B represents one embodiment of a patient interface for NPLT when optoacoustic waves are generated inside the tissue by the pulsed light.

FIG. 1B represents one embodiment of a patient interface (20) for NPLT wherein optoacoustic waves are generated inside a tissue by pulsed light. The patient interface has one or more optical fibers (24) to direct pulsed light to the tissue. For certain indication including transcranial NPLT, the tips of the fibers may protrude from the patient interface to provide better light delivery through hairs (in such a fiber-optic "brush" wherein optical fibers can penetrate between hairs and deliver more light to the scalp).

Figure 1C:
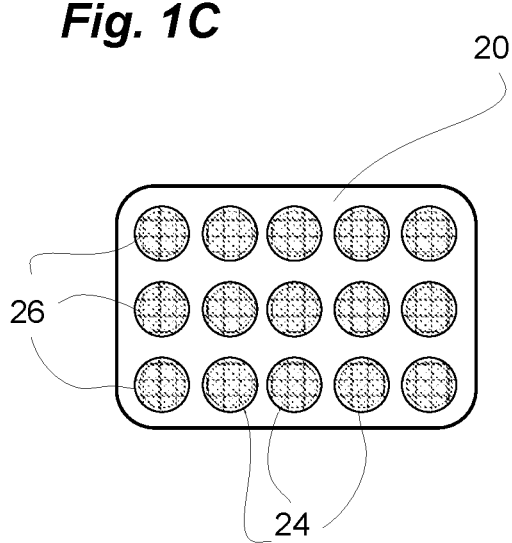
FIG. 1C represents another embodiment of a patient interface for generation of optoacoustic waves in an optical absorber by the pulsed light.
Figure 1D:
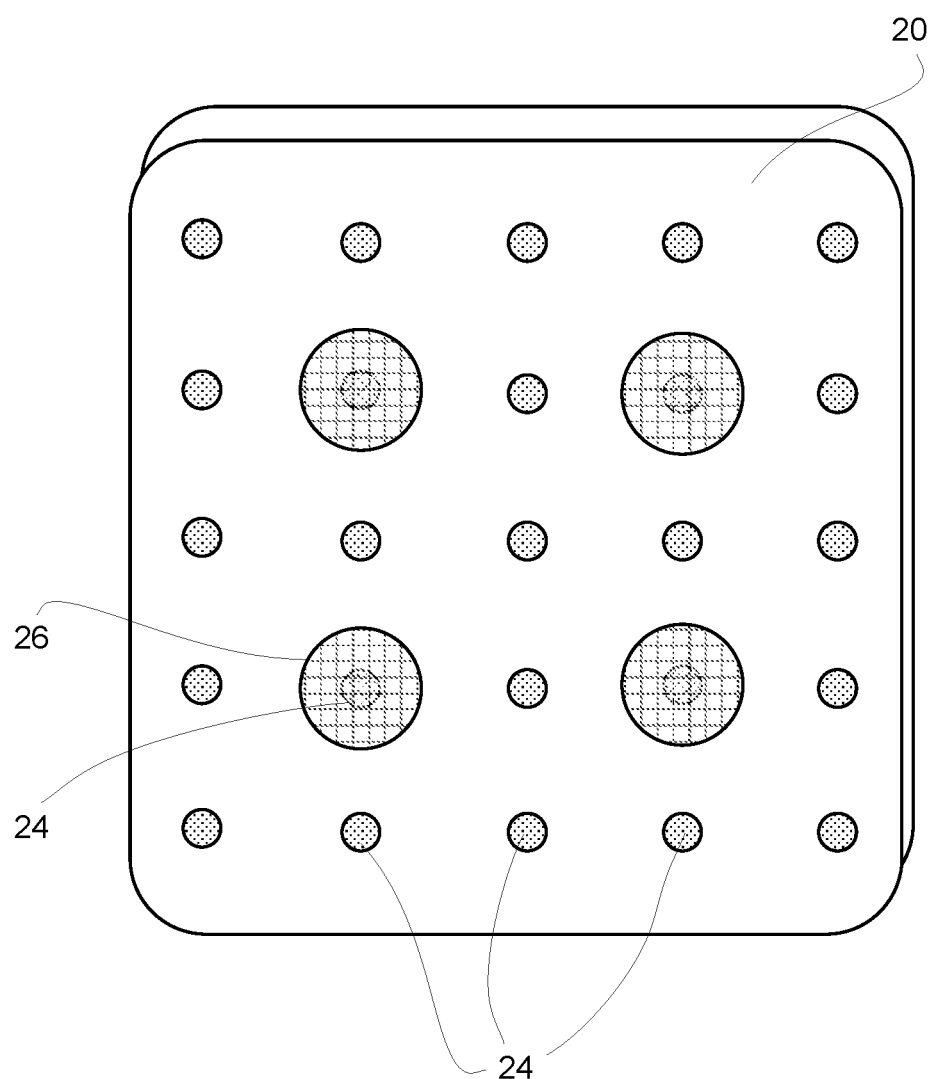
FIG. 1D represents another embodiment of a patient interface for NPLT when optoacoustic waves are generated both inside the tissue and in an optical absorber outside of the tissue.

FIG. 1C represents an embodiment of a patient interface (20) wherein optoacoustic waves are produced by a plurality of optical absorbers (26) overlying all of a plurality of optical fibers (24). The pulse light is absorbed by the absorbers and generates optoacoustic waves outside of tissue. The optoacoustic waves generated in the absorber propagate to the tissue and provide an optoacoustic (ultrasound) wave only mode of therapy. FIG. 1D represents another embodiment of a patient interface (20) for NPLT wherein optoacoustic waves are generated both inside the tissue and outside the tissue via a plurality of optical absorbers (26) overlying some but not all of the optical fibers (24). This patient interface provides an option of varying proportions of optoacoustic waves generated inside and outside of tissue.

Depending on the type, severity, and stage of the disease, NPLT with one or more of these patient interfaces can provide better therapeutic effect and treatment outcome. It should be noted that other light delivery systems (articulated arm, etc.) can be used. Moreover, delivery of light may be performed directly from the pulsed light system without console mounted light delivery systems, for instance, pulsed light systems (such as pulsed laser diodes or LEDs) may be attached to the patient's tissue.

Using an embodiment of an NPLT system, compelling evidence has been generated that transcranial delivery of NPLT limits the immediate, short- and long-term effects that follow traumatic brain injury (TBI), including post-injury neural and immune cell overstimulation, inflammation, cell loss and neurologic and vascular dysfunction as shown in the experimental data presented in FIGS. 2-11.

Specifically, we have shown that in rodent models of TBI, NPLT confers several benefits including:
- prevention of vestibulomotor and cognitive dysfunctions,
- protection of cortical neurons by up-regulating the expression of the neurotrophic factor BDNF and of the anti-apoptotic protein Bcl2 while inhibiting caspase 3-mediated apoptotic death,
- reduction of inflammation by inhibiting microglia activation in the brain,
- reduction of oxidative stress and DNA damage, and
- increases in neurogenesis by increasing the proliferation of neural stem cells and the generation of new neurons.

The therapeutic value of the disclosed system is unique because, by generating short, high-energy pulses of near-infrared light, it generates low intensity optoacoustic (ultrasound) waves thus combining the beneficial effects of near infrared light and low intensity ultrasound therapy. In fact as shown herein, optoacoustic (ultrasound) waves, generated by a short pulse near infrared laser, increased proliferation of hippocampus neural stem cells (NSC) both in vivo and in vitro in part by reducing the levels of specific regulatory microRNAs (miRNAs).

It is additionally shown that only the combination of near infrared light and ultrasound waves, and not near infrared light alone, is able to increase the level of regulatory miRNAs that result in the generation of new neurons. Thus, the system can be used to selectively modulate neurogenesis by increasing the number of neural progenitors and their neuronal differentiation.

This unique feature of the disclosed system is highly innovative and of significant clinical relevance. In fact, when administered during the acute and sub-acute phase after brain injury, when neural stem cells are known to proliferate but fail to differentiate into neurons, NPLT can be used to increase the generation of neurons. On the other hand, when administered in the chronic phase following brain injury, when impaired neurogenesis is primarily due to reduced number of NSC in the hippocampus, NPLT can be used to stimulate NSC proliferation.

The optoacoustic waves generated by our system are different from conventional ultrasound waves generated by standard ultrasound systems because the optoacoustic waves have a wide frequency range. This may provide additional therapeutic effect compared to the standard ultrasound waves.

Based on the data provided herein, it can be concluded that, depending on the type, severity, and stage of disease, light and optoacoustic wave doses can be varied to provide highly efficient therapy. Moreover, if a higher optoacoustic wave dose is needed, one can use optical absorbers on the skin surface that will generate optoacoustic waves at higher amplitudes that those generated naturally within tissues by the light pulses. The absorbers include, but are not limited to liquid, solid state (metal, ceramics, semiconductors, plastics, glass) and gas state absorbers. To provide high Gruneisen coefficient, it is preferable in certain circumstances to use liquid absorbers, including but not limited to alcohol or water-containing liquids with strongly absorbing chromophores. For instance, alcohol-based liquids have higher Gruneisen coefficient than that of water-based liquids or solid state absorbers.

Moreover, to provide even more efficient generation of optoacoustic waves, one can use phase transition in the absorber, including but not limited to liquids at critical temperature that under pulsed light irradiation produce optoacoustic waves with very high amplitude due to transition from the liquid phase to the gas phase (bubble formation/evaporation).

Absorbers with a specific pattern and shape can provide: light with ultrasound, light without ultrasound, or ultrasound only irradiation of tissues for better therapeutic effect. These modes of irradiation can be switchable and, depending on the type, severity, and stage of the disease, can be used for best therapeutic effect.

In one study described herein, a well-established rodent model of blast-induced neurotrauma was demonstrated. The model is known to reproduce many features associated with clinical sequelae experienced by both military personnel and civilians exposed to high pressure waves generated by explosion devices and was used to test the therapeutic potential of the novel system disclosed herein for non-invasive transcranial delivery of short laser pulses of near-infrared light that generate optoacoustic waves. In contrast the system provided herein, photobiomodulation and LLLT utilizes either continuous wavelength (CW) light or long (tens of milliseconds) pulses that do not provide the stress-confined condition and cannot generate optoacoustic waves.

In one embodiment described herein, light pulses with duration shorter that 10 ns (for instance, picosecond or femtosecond pulses) are used for the NPLT because they generate optoacoustic waves in tissues. Moreover, pulses with duration of the order of hundreds of nanoseconds produce optoacoustic waves with high efficacy in tissues. Therefore, NPLT therapeutic effect can be achieved by pulses with durations in the range from femtoseconds to microseconds.

Although pulse energy and average power exemplified here are low, the short pulses have high peak intensity. This may produce multi-photon effects including two-photon photochemical and photobiological effects. Moreover, irradiation by short pulses of tissue micro-volumes with higher absorption may result in local heating of these volumes. Moderate local heating by the laser pulses used in our study may have biomodulation/therapeutic effects as well.

Other previously tested devices that deliver LLLT utilize either continuous wave light or long (tens of milliseconds) pulses that do not provide the stress-confined conditions necessary to generate optoacoustic waves. In contrast, as exemplified herein, short laser pulses are used to generate optoacoustic waves; thus, the injured tissue was irradiated by near-infrared light and ultrasound (optoacoustic) waves simultaneously.

Because low-level ultrasound has therapeutic effects, both light and ultrasound can contribute to the neuroprotective effects produced by NPLT. It appears from the data that the light pulses and optoacoustic waves have synergistic effects that result in more efficient neuroprotection. It should also be noted that optoacoustic waves travel deeper into the brain than near-infrared light, which has been shown to reach a depth of only 40-50 mm in the human brain.

This penetration is expected to result in a stronger therapeutic effect as compared to LLLT. The data provided herein show that transcranial application of NPLT delivered one hour after blast exposure prevents vestibulomotor dysfunctions, significantly prevents ongoing neuronal cell death in the brain cortex, and decreases associated cognitive dysfunctions that occur after blast injury. Previous reports have shown that transcranial delivery of low level near-infrared light generated by light emitting diode ("LED") or laser sources improved the performance of experimental animals subjected to memory-related tasks in rodent models of TBI. However, the device and method provided herein is the first to provide a therapy that combines low-level near-infrared light and ultrasound (optoacoustic) waves to show a significant benefit in models of TBI. Specifically, the data demonstrate the ability of transcranial NPLT to significantly reduce both vestibulomotor and cognitive dysfunction that represent a common and severely debilitating clinical manifestation in TBI individuals.

As demonstrated herein, NPLT surprisingly makes neurons resistant to cell death by inducing upregulation of neuroprotective genes (BDNF and Bcl-2) and downregulation of pro-apoptotic genes (BAX and caspase 3). Most importantly, the data provided herein confirm that significantly fewer cortical neurons undergo apoptosis, as evidenced by the lack of caspase 3 activation, one week after blast injury to the brain. Thus, the data support the therapeutic efficacy of NPLT in preventing neuronal cell death that is known to occur during the secondary phase following TBI. Moreover, it is shown that the protective effect of NPLT is not limited to the most external cortical structures but extends to deeper structures of the brain, including the hippocampus. The hippocampus plays a critical role in memory and learning and is one of the brain areas most affected by TBI.

BDNF is an important neurotrophin known to support hippocampal neurons. While BDNF expression in the hippocampus is significantly reduced after blast injury, in NPLT-treated rats its expression level is comparable to uninjured control rats. Remarkably, this finding correlates with improved performance of NPLT-treated rats in the working memory paradigm of the Morris water maze test. The results further support a therapeutic role of NPLT in preserving hippocampal-dependent cognitive functions after blast-induced neurotrauma.

The hippocampus is one of the brain areas in which neurogenesis is known to occur throughout life. Neural stem cells (NSCs) located in the subgranular zone of the dentate gyms of the hippocampus proliferate to generate more NSCs and give rise to neuronal progenitor cells that migrate within the granular cells layer, where they become mature neurons. Much evidence in the literature points to a critical role of neurogenesis in supporting cognitive function. Specifically, while a reduction in the numbers of NSC in the DG is associated with impaired hippocampus-dependent functions (learning and memory), an increase in NSC numbers contributes to improved learning and memory. In certain embodiments, NPLT is utilized to improve hippocampus-dependent functions in age-related (presenile) dementia, in stroke victims, in patients with neurodegenerative diseases, in cognitive decline in the elderly as a consequence of atherosclerosis and in treatment of patients experiencing cognitive decline caused by normal pressure hydrocephalus.

As exemplified herein, it is shown that NPLT increases the number of proliferating (BrdU-incorporating) NSCs in the DG of the hippocampus after acute brain injury. Importantly, a significant reduction of TBI-induced inflammatory response was observed in NPLT-treated rats. Activation of microglia is a well-known sequelae of brain injury in humans associated with cognitive dysfunctions and early onset of neurodegenerative disorders.

In the data presented herein, use of device and method disclosed herein resulted in significantly less abundant activated $CD68^{pos}$ microglia cells in the cortex of rats treated with NPLT as compared to untreated TBI-injured rats seven to fifteen days after brain injury. Inflammation mounts in the hours and days following brain injury in response to cell damage. As demonstrated herein, when NPLT was administered one hour after TBI may have provided neuroprotective properties rather than a direct anti-inflammatory effect. In certain embodiments, NPLT is applied to provide neuroprotective effects in closed head injury as well as both hemorrhagic and ischemic stroke.

The transcranial application of the novel NPLT described herein, combining the benefits of both near-infrared light and low intensity ultrasound waves, provides at least the following beneficial effects in rodent models of TBI: it significantly reduces neuronal cell death and neuroinflammation, increases both neurotrophin expression and proliferation of neural progenitors in the hippocampus, and provides significant vestibulomotor and cognitive improvements. Due to increased penetration in the brain of the ultrasound component, NPLT has greater translational value for the treatment of TBI survivors compared to near-infrared light alone and prompts further studies to test this promising therapy.

Nano-Pulsed Light Diagnostics and Therapy (NLPDT): Optoacoustic waves may also be used for biomedical imaging, monitoring, and sensing (e.g. for optoacoustic diagnostics). In certain embodiments, optoacoustic theranostics are provided that combine the therapeutic capabilities of optoacoustics with diagnostics, e.g. Nano-Pulsed Light Diagnostics and Therapy (NPLDT). Light pulses are used in NPLDT for diagnosis of the disease, monitoring during NPLT, and assessment of therapeutic response during and/or after NPLT.

While the making and using of various embodiments of the present invention are discussed in detail below, it should be appreciated that the present invention provides many applicable inventive concepts which can be employed in a wide variety of specific contexts. The specific embodiments discussed herein are merely illustrative of specific ways to make and use the invention and do not delimit the scope of the invention.

EXAMPLE 1

Cognitive and Motor Function Testing

In one embodiment, in order to test the effect of NPLT on TBI-induced vestibulomotor and cognitive dysfunctions, rats were subjected to beam walk and beam balance tests on post injury days (PIDs) 1-3 and on the working memory paradigm of the Morris water test on PIDs 6-10 and PIDs 11-15.

Male Sprague-Dawley rats (300-350 g) were subjected to blast-induced neurotrauma using a Vandenberg device that produces a combined blast over/underpressure that is followed by a blunt impact caused by the venting gas jet or to fluid percussion injury. One hour later the subjects were treated with NPLT for 5 minutes. In one embodiment, the NPLT treatment utilized a tunable optical parametric oscillator that generated nanosecond pulses in the near infra-red spectral range (from 680 to 950 nm) energy of up to 15 mJ, with duration of 7 ns, repetition rate of 20 Hz, producing low-level, wide-band, MHz optoacoustic (ultrasound) waves.

In another embodiments, the treatment utilized an optical parametric oscillator that generated short (10 ns) pulses of near-infrared light (808 nm) at energy of up to 15 mJ and pulse repetition rate of 20 Hz. The laser pulses were delivered to the intact rat head using a specially developed fiber-bundle system. The pulse energy and spot size on the rat head were 5 mJ and 3 mm, respectively. These pulses generate low-level optoacoustic waves that travel deeper into the brain. Rats were treated one hour after TBI for a duration of 5 minutes to provide a dose of 300 $J/cm^2$, which is similar to that used for the LLLT with continuous wave light. A separate group of rats was subjected to TBI but did not receive the treatment (indicated as BLAST or TBI). SHAM rats were anesthetized but not subjected to blast injury.

Vestibulomotor testing was conducted using beam balance and beam walk testing. Rats underwent two training sessions and one pre-injury assessment. For beam balance, the rats were trained to balance for 60 seconds on a short wooden beam (50×1.5×4 cm) raised 90 cm off the floor. Once the rats were able to remain on the beam, they were evaluated for three consecutive trials per session and rated using a six point scale, with lower score indicating a better performance. For beam walk testing, animals were trained to traverse a wooden beam (100×2.5×4.0 cm) elevated 1 meter above the floor. Four steel pegs were equidistantly spaced along the top and a darkened goal box was positioned at the far end of the beam. Once trained, the rats were timed during three consecutive trials with time to reach the goal box as the primary endpoint. On the day of injury rats underwent a pre-injury assessment.

Figure 2A:
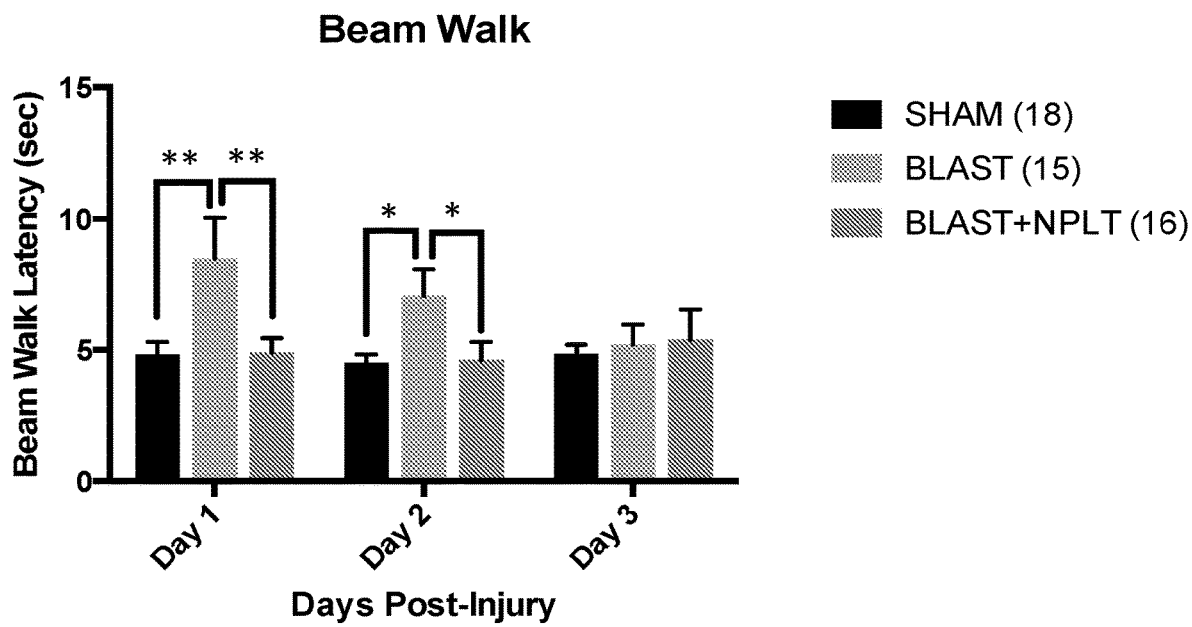
FIG. 2A represents vestibulomotor testing post-injury days (PID) 1 and 2 compared to rats that were sham injured or received BLAST+NPLT using the beam walk test. In the beam walk test, rats that received blast injury showed longer latencies to traverse the beam on PIDs 1 and 2 compared to rats that were sham injured or received blast plus NPLT treatment. Two-way ANOVA revealed a significant overall effect of treatment ($P<0.01$). Post-hoc Fisher's multiple comparisons test revealed **$P<0.01$ BLAST vs SHAM on PID 1 and *$P<0.05$ BLAST vs BLAST+NPLT on PID 2.
Figure 2B:
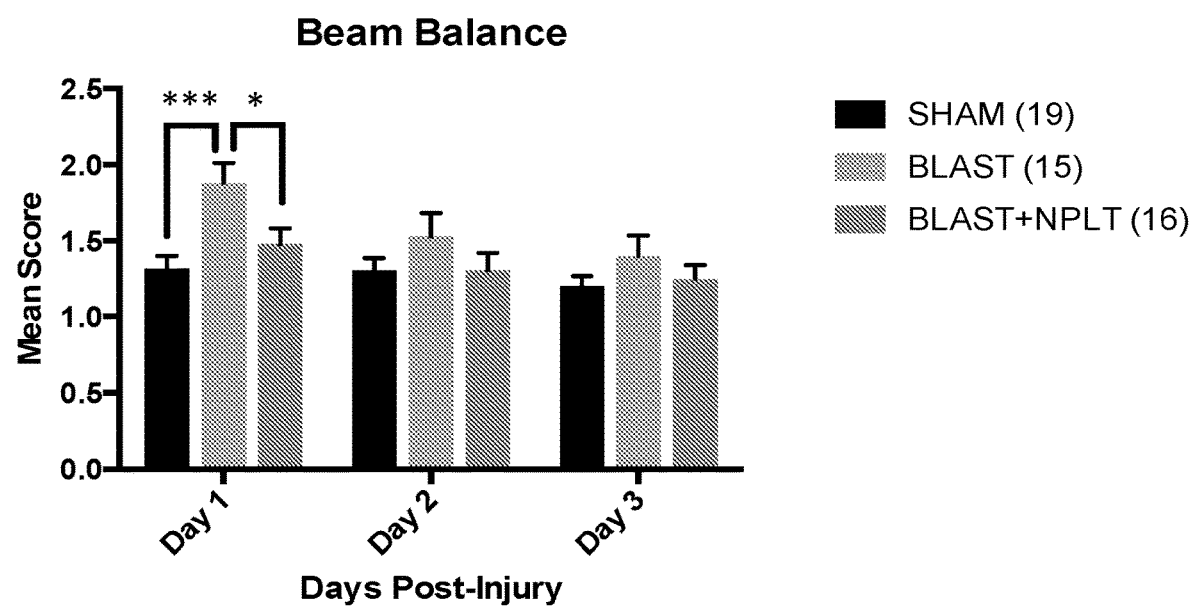
FIG. 2B represents vestibulomotor testing post-injury days 1 and 2 compared to rats that were sham injured or received BLAST+NPLT in the beam balance test. In the beam balance test, rats that received blast injury had higher scores on PID 1 compared to rats that received sham injury or blast plus NPLT treatment. Two-way ANOVA revealed a significant overall effect of treatment ($P<0.001$) and time after injury ($P<0.001$). Post-hoc Fisher's multiple comparisons test revealed ***$P<0.001$ BLAST vs SHAM; * $P<0.05$ BLAST vs BLAST+NPLT on PID 1. The number of animals is shown in parenthesis.

In the beam balance test, rats that received blast-injury scored significantly higher on PID 1 as compared to SHAM controls. As previously mentioned, a lower score indicates a better performance. On the other hand, blast-injured rats that received NPLT 1 h after injury received scores similar to SHAM rats and significantly lower than blast-injured rats (FIG. 2A). In the Beam Balance Test, rats that received BLAST had higher scores on post-injury day 1 compared to rats that received sham injury or BLAST+NPLT (FIG. 2B). Data is mean +/− SE. * $P<0.05$ vs SHAM: ˆ $P<0.05$ vs BLAST+NPLT.

On the beam walk test, blast-injured rats took significantly longer to cross the beam (longer latency) on PIDs 1 and 2 as compared to both SHAM controls and blast-injured rats that received NPLT (BLAST+NPLT) (FIG. 2A).

EXAMPLE 2

Working Memory Testing

The Morris Water Maze (MWM) was used to assess working memory, as described in detail by Sell et al. (Sell, SL, et al. Persistent Behavioral Deficits in Rats after Parasagittal Fluid Percussion Injury. *J Neurotrauma* 34 (2017) 1086-1096). Briefly, the experimental animals were placed in a tank filled with water to a level that was 2 cm higher than a hidden platform. Rats were assigned four starting points and four platform locations in a balanced order to avoid starting points too close to the platform. For Trial 1, rats were placed in the tank and allowed 120 seconds to find the platform. Once on the platform, the rats were allowed 15 seconds to rest and then were placed in the tank again from the same starting point to begin Trial 2. They were again allowed 120 seconds to find the platform. Rats were rested 4 min in a heated enclosure before starting a second pair of trials which used different platform and starting locations. Rats received four pairs of trials daily for five consecutive days. All rats received the same sequence of starting points and platform locations.

Figure 3:
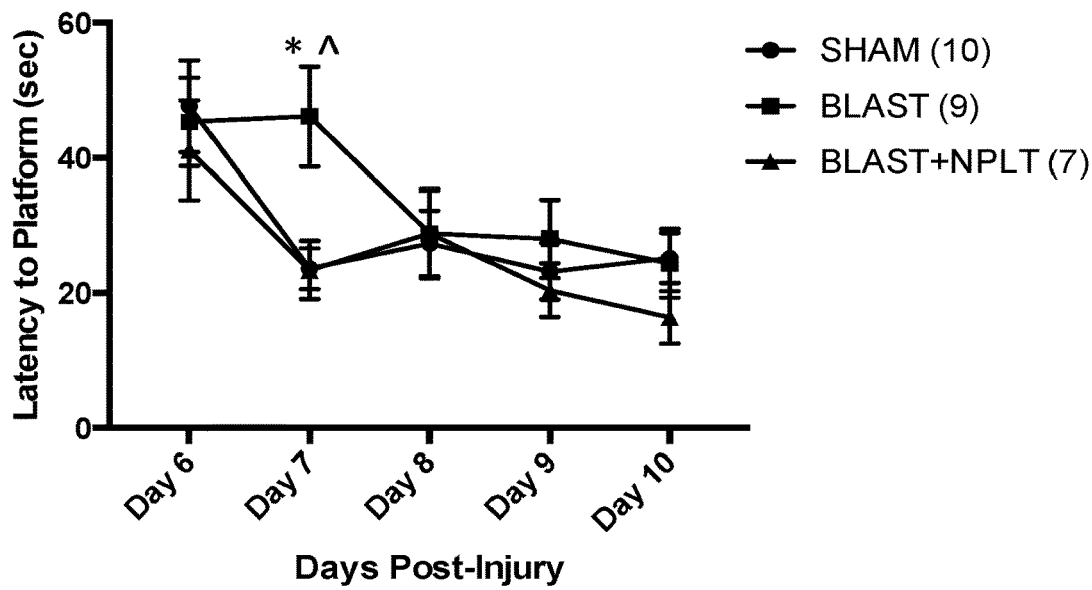
FIG. 3 represents working memory testing in rats that were sham injured or received BLAST+NPLT. Rats were tested in the working memory paradigm of the Morris Water Maze test on PIDs 6-10. Only data from Trial 2 is shown. Two-way ANOVA revealed a significant overall effect of treatment ($P<0.05$) and of time after injury ($P<0.0001$). Post-hoc Tukey's multiple comparisons test revealed **$P<0.01$ BLAST vs SHAM and ^$P<0.05$ BLAST vs BLAST+NPLT on PID 7. Data is mean +/− SEM. Number of animals is shown in parenthesis.
Figure 4A:
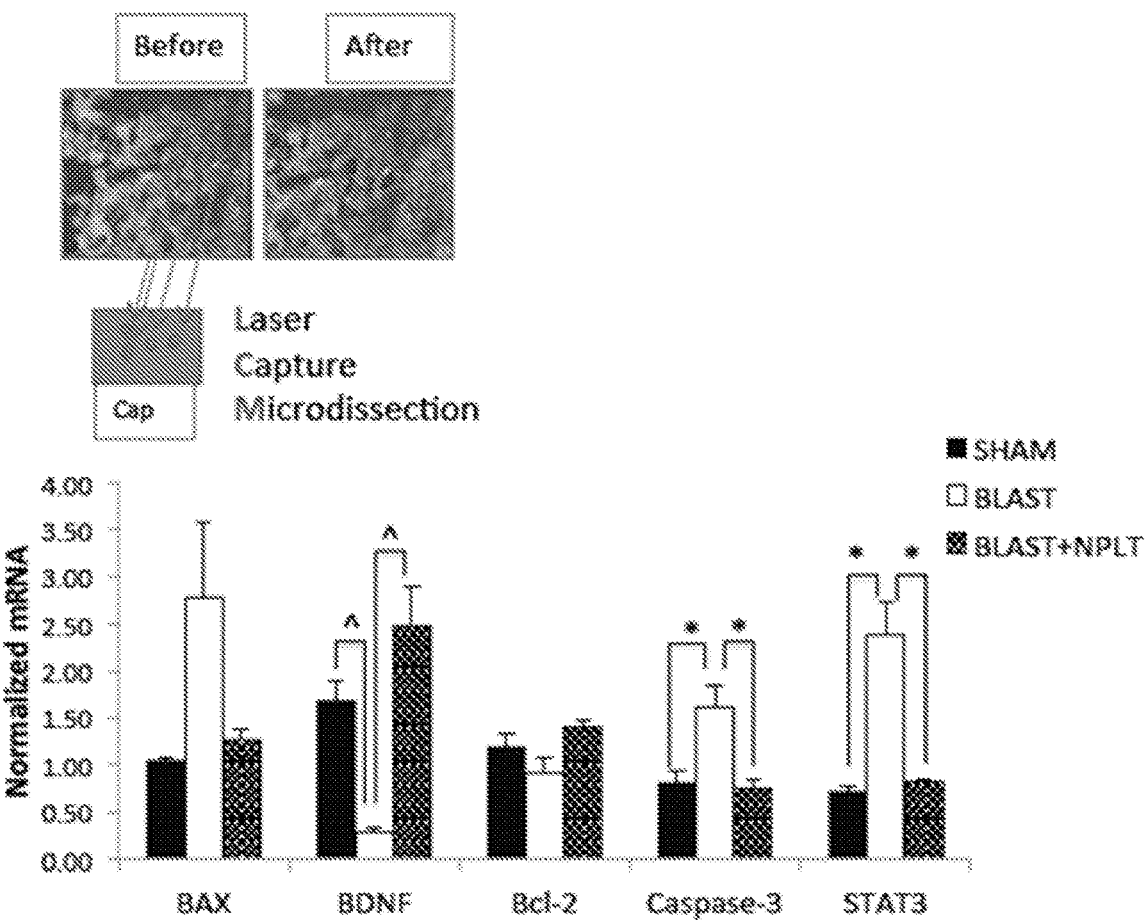
FIG. 4A represents conduct of a laser capture microdissection analysis with summary of results of mRNA expression for BAX, BDNF, Bcl-2, Caspase-3 and STAT3 in the prefrontal cortex of rats that were sham injured or received BLAST+NPLT. Experimental animals were euthanized on PID 3 and the brains removed and processed for laser-capture micro-dissection (LCM) of cortical neurons. The expression of select mRNAs was measured by qRT-PCR analysis. Data was normalized to GAPDH expression and expressed as mean +/− SEM. N=4 for SHAM; N=3 for BLAST and BLAST+NPLT. * $P<0.05$ one-way ANOVA followed by Fisher's multiple comparisons test.
Figure 4B:
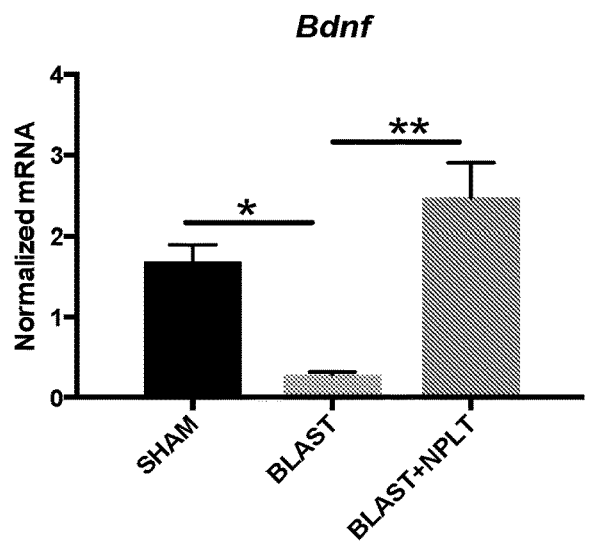
FIGS. 4B-4F detail the data shown in FIG. 4A.
Figure 4C:
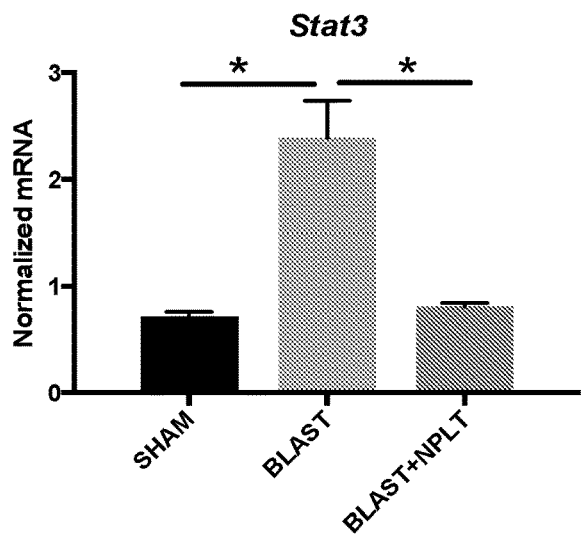
Figure 4D:
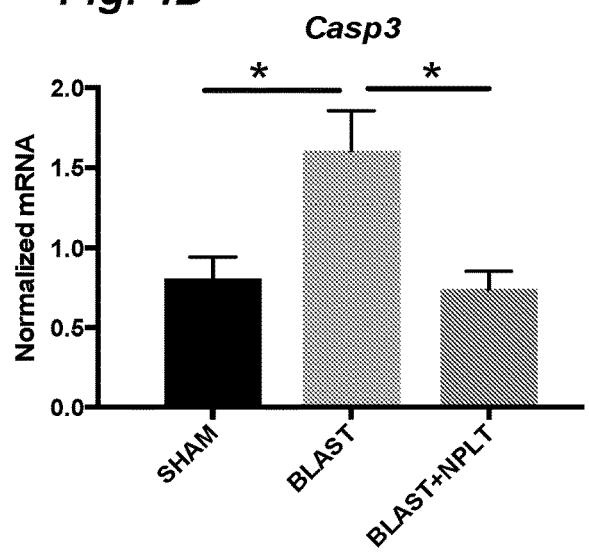
Figure 4E:
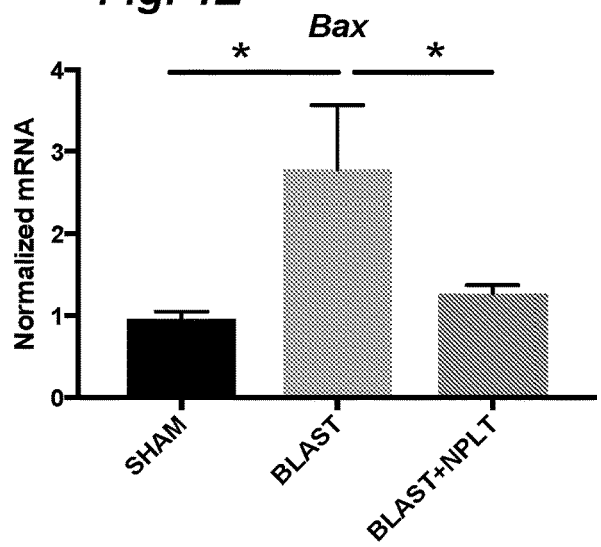
Figure 4F:
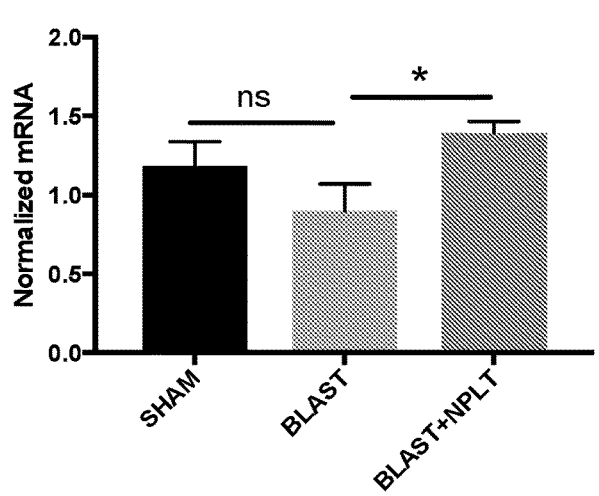

In one test, male Sprague-Dawley rats (300-350 g) were subjected to blast-induced neurotrauma using a Vanderberg device and 1 hour later treated with NPLT as described in Example 1 for 5 minutes (BLAST+NPLT). A separate group of rats was subjected to blast injury but did not receive the treatment (BLAST). SHAM rats were anesthetized but not subjected to blast injury. The rats were tested in a Morris Water Maze variation for working memory assessment. The rats that received BLAST took significantly longer to find the hidden platform on post-injury day 7 (PID 7) as compared to SHAM treated rats and to rats that received BLAST+NPLT (FIG. 3). Data is mean +/− SE. *P<0.05 vs SHAM: ^ P<0.05 vs BLAST+NPLT.

EXAMPLE 3 mRNA Expression

Laser Capture Microdissection ("LCM") was utilized to prepare samples for analysis of mRNA expression. At the appropriate time, rats were euthanized and the brains were dissected out, rapidly frozen in dry ice, and stored at −80° C. To prepare for cryo-sectioning, tissues were frozen in OCT mounting medium, 10 µm coronal brain sections were cut on a cryostat (Leica Microsystems CM1850), and mounted on superfrost clean glass slides. Sections were stained with 0.001% Fluoro-Jade (Histo-Chem, Inc, Jefferson, Ark.), a marker for neuronal injury, and counterstained with 1% cresyl violet (a Nissl stain). All solutions were prepared with RNase-free water, and the cresyl violet and the Fluoro-Jade (FJ) were sterile filtered immediately before use.

LCM was performed using a PixCell IIe laser capture microscope with an infrared diode laser (Arcturus Engineering, presently Arcturus/ LifeTechnologies/Thermo-Scientific, Carlsbad, Calif.). The smallest laser spot size (7.5 µm) was used with a power setting of 75-100 mW and a pulse duration of 0.35-0.75 ms (settings were adjusted, as necessary, for optimum capture of the cells). Uninjured (FJ-negative) neurons from the cortex and hippocampus were captured on a thermoplastic film of separate CapSure Macro LCM caps (Thermo-Fisher Scientific, Carlsbad, Calif.). They were placed into a 0.5 ml tube containing 100 ul of Lysis buffer (Ambion/Thermo-Scientific), vortexed, and stored at −80° C. until isolation of total RNA.

Total RNA was isolated using the RNA Aqueous Micro kit (Ambion/Thermo Scientific) according to the manufacturer's protocol before DNase treatment at 37° C. for 20 min to remove any traces of genomic DNA. The concentration and quality of total RNA was assessed using an Agilent Bioanalyzer with the RNA6000 Pico Lab Chip (Agilent Technologies). Afterward, 1 ng of total RNA was reverse transcribed using the High Capacity cDNA Reverse Transcription Kit (Applied Biosystems/Thermo-Scientific) according to the manufacturer's protocol. Taqman PreAmp master mix kit (Applied Biosystems/Thermo-Scientific) was used to pre-amplify cDNA to increase the quantity of specific cDNA targets including BDNF, STATS, CASP3, Bcl-2, BAX, GAPDH. The cDNA was pre-amplified for 14 cycles with a thermal profile of 1 cycle at 95° C. for 10 min and 14 cycles at 95° C. for 15 s/60° C. for 4 min. Pre-amplification products were diluted 1:20 with 1× TE buffer before proceeding to Quantitative PCR. Quantitative Real-Time PCR was performed on a MX3000P instrument (Agilent Technologies) with Taqman chemistry probes (Applied Biosystems/Thermo-Scientific) with the following thermal profile: 50° C. for 2 min (1 cycle), 95° C. for 10 min (1 cycle), 95° C. for 15 s/60° C. for 1 min (45 cycles). Each PCR reaction was performed in triplicate. Normalization to GAPDH, a housekeeping gene, was performed by calculating the ACt for each gene of interest (GOI). This calculation involves subtracting the Ct value of the gene of interest from the Ct value of GAPDH. All data from the PCR was collected and analyzed by the MXPro software (provided by Stratagene with purchase of Mx3000 Multiplex Quantitative PCR System) and ΔΔCT fold changes were calculated, graphed, and plotted in Excel.

In order to determine whether NPLT can protect cortical neurons from dying in the days following the initial blast insult, on PID 3 the expression of mRNA encoding for the following genes was measured: neurotrophic factor BDNF and the transcription factor STAT3 (known to be upregulated in response to injury), anti-apoptotic (BCL2) and pro-apoptotic (BAX and CASP3) proteins using qRT-PCR in laser-captured cortical neurons. In one assay, male Sprague-Dawley rats (300-350 g) were subjected to blast-induced neurotrauma using the Vanderberg device and 1 hour later treated with NPLT for 5 minutes (BLAST+NPLT) in accordance with Example 1. A separate group of rats was subjected to blast injury but did not receive the OA treatment (BLAST). SHAM rats were anesthetized but not subjected to blast injury. Cortical neurons were laser-captured on day 3 post-injury and quantitative RT-PCR analysis was performed for genes known to be involved in inducing cell death (BAX and caspase 3, CASP3), for the transcription factor STAT3, and for the neurotrophic factor BDNF (FIG. 4). Data is expressed as average +/− SE. N=4 for sham; N=3 for BLAST and BLAST+NPLT. One way ANOVA with post hoc Student's T-test analysis was conducted.

In order to selectively measure the expression of these mRNAs in surviving cells, the sections were stained with FluoroJade (FJ: a marker of neuronal injury) and laser-captured only $FJ^{neg}$ neurons. In $FJ^{neg}$ cortical neurons isolated from blast-injured rats, it was found that the mRNAs levels for STAT3, BAX, and CASPASE-3 were significantly higher as compared to both sham and NPLT-treated blast-injured rats, while the levels of BDNF and Bcl-2 were lower.

EXAMPLE 4

Tissue Processing and Immunofluorescence Analysis

At the appropriate time point after blast or sham injury, rats were euthanized, brains were dissected out, rapidly frozen in dry ice, and stored at −80° C. To prepare for cryo-sectioning, tissues were frozen in OCT mounting medium and 10 µm coronal brain sections were cut on a cryostat (Leica Microsystems CM1850). Sections were mounted on superfrost clean glass slides (Superfrost Plus, Thermo Fisher Scientific Inc., Marietta, Ohio) and stored at −80° C. until ready to use. For immunofluorescence analysis, the sections were fixed in ice-cold 10% buffered formalin and incubated in PBS containing 10% normal goat serum and 0.3% Triton X-100 for 30 min at room temperature. The sections were incubated with primary antibodies diluted in PBS containing 1.5% normal goat serum overnight at 4° C. They were then incubated with secondary antibodies (594- and 488-Alexa-conjugated, Invitrogen Co., Carlsbad, Calif.; 1:400 dilution in PBS with 1.5% normal goat serum) for 1 h at room temperature. After washing in PBS, the sections were rinsed in tap water and coverslipped with mounting media containing DAPI (Vector laboratories, Burlingame, Calif.). Primary antibodies were as follows: rabbit anti-cleaved caspase-3 (1:200; R&D), mouse anti-NeuN (1:100; Millipore), rabbit anti-CD68 (1:200; Abcam). Fluorescent images were acquired with an Olympus BX51 microscope equipped with a cooled CCD camera.

For BrdU detection, frozen sections were fixed in ice-cold 10% formalin for 30 min. After washing in 0.1 M PBS (pH 7.4), sections were incubated in 1N HCl solution for 30 min at 37° C. and then washed in 0.1 M borate buffer (pH 8.5). Endogenous peroxidase activity was blocked by incubation in 1.5% hydrogen peroxide in distilled $H_2O$ for 30 min. The sections were blocked and permeabilized in 5% normal goat serum and 0.3% triton X-100 in PBS for 30 min. This step was followed by incubation with the primary antibody (ms anti-BrdU; 1:100 DAKO) in PBS overnight at 4° C. The following day, after washing in PBS, sections were incubated with secondary antibody (biotinylated goat anti-mouse, ABC mouse kit, Vector laboratories) before incubation with an avidin-biotin complex (ABC kit, Vector laboratories) according to the manufacturer's instructions. Staining was visualized by incubating the sections with DAB substrate for 10 min. After washing for 5 min in tap $H_2O$, a light counterstain using Hematoxylin QS (Vector laboratories) was performed. Sections were dehydrated in graded ethanol solutions of increasing concentrations, cleared in xylene, and coverslipped with Permount (Sigma). Images were taken with an Olympus BX51 microscope equipped with a cooled CCD camera.

Active Caspase$3^{pos}$/NeuN$^{pos}$ cells, CD68$^{pos}$ cells, and BrdU$^{pos}$ cells were counted in every fifth section of a series of 10 μm coronal brain sections (total of 5-10 sections per animal). Using ImageJ software, counting was performed by two independent investigators who were blinded to the experimental groups. Statistical analysis of data was expressed as the mean+/− standard error of the mean (SEM). Statistical analysis was performed with the aid of a proprietary software (GraphPad Prism 7). Results were considered significant for P values<0.05.

Figure 5:
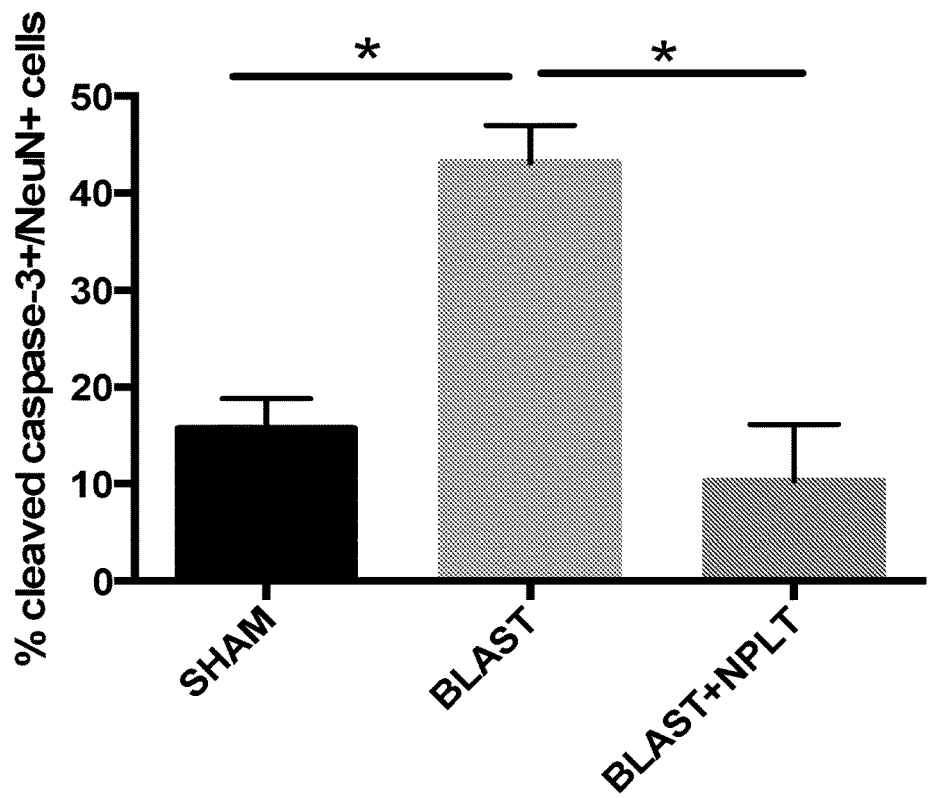
FIG. 5 shows quantitative analysis of the number of active caspase 3-positive neurons in the cortex demonstrating that NPLT prevents apoptotic cell death in cortical neurons. Caspase 3 expression was examined in NeuN positive cells. Experimental animals were euthanized on PID 3 and the brains processed for immunofluorescence analysis.

Caspase 3 expression in NeuN positive cells was also determined. Brain sections at the level of the cortex stained with an antibody against the neuronal marker NeuN (red) and active caspase 3, a marker of apoptotic cell death (green). Nuclei were counterstained with DAPI (blue). Quantitative analysis of the number of active caspase 3-positive neurons showing that NPLT prevents the increase of apoptotic cells in the cortex is shown in FIG. 5. Cells were counted using Image J software. N=3 rats/group. * P<0.05 by ANOVA followed by Student's T-test.

Figure 6A:
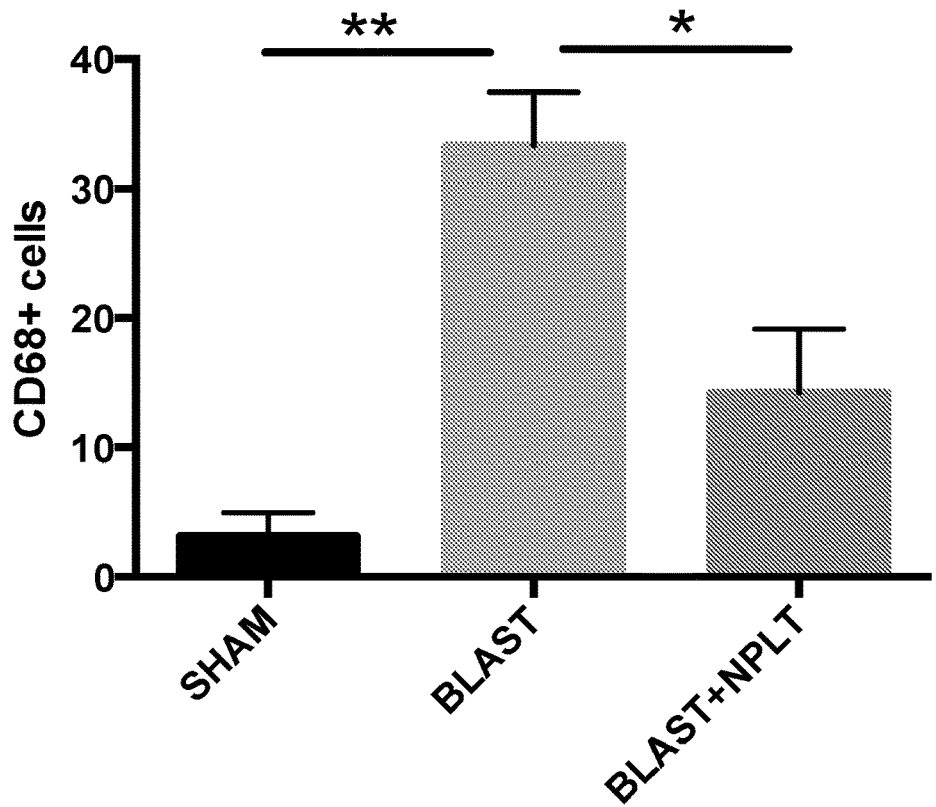
FIG. 6A shows quantification of the number of $CD68^{pos}$ cells in the cortex. N=3 rats/group. *$P<0.05$; **$P<0.01$ one-way ANOVA followed by Tukey's pot-doc multiple comparisons test. Microglia activation on PID 10 was analyzed by immunofluorescence. Brain sections at the level of the cortex were stained with an antibody against CD68 (a marker of activated microglia) and nuclei are counterstained with DAPI.

The onset of neuroinflammation is a major hallmark of the acute and chronic sequelae of brain injury. Inflammation was analyzed 10 days after blast injury by immunofluorescence using a specific antibody against CD68, a marker of activated microglia. See FIG. 6A. Numerous CD68$^{pos}$ cells were observed in the cortex of blast-injured rats, while few or no CD68$^{pos}$ cells were observed in both sham and blast-injured rats that received NPLT (FIG. 6A). Quantification studies confirmed that the number of CD68$^{pos}$ microglial cells was significantly lower in the cortex of NPLT-treated blast-injured rats as compared to untreated blast-injured rats.

Rat brain sections were also stained with an antibody against CD11b (a marker for activated microglia) in the brains of rats that were sham injured or received BLAST+ NPLT with similar results to that found with the CD68 analysis.

Figure 6B:
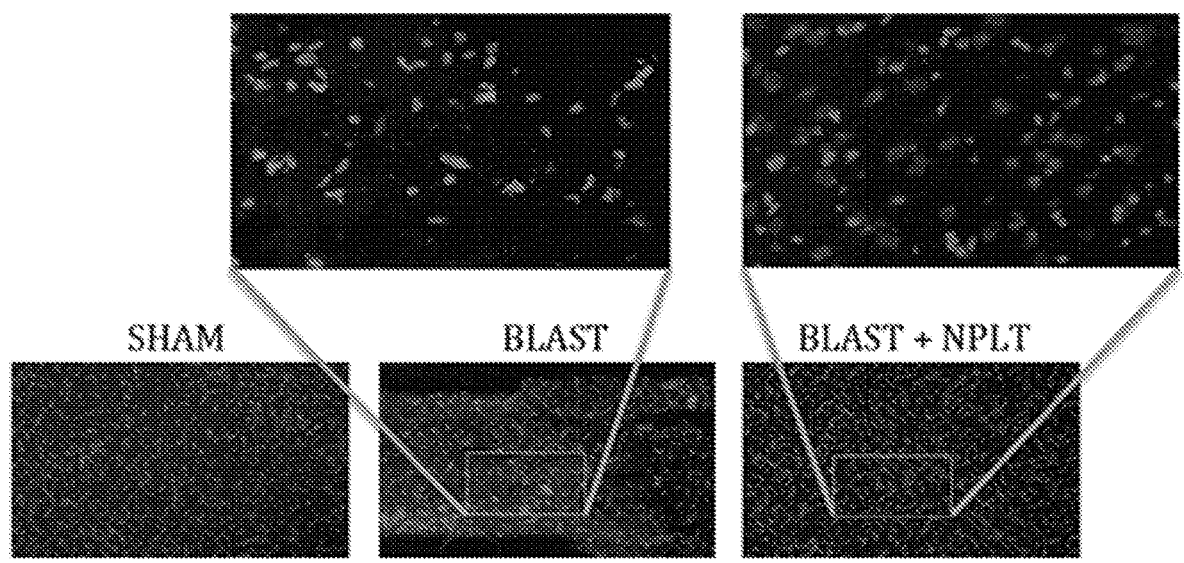
FIG. 6B shows representative images of rat brain sections stained with an antibody against 8-hydroxy-2'-deoxyguanosine (a marker of oxidative damage to DNA).

FIG. 6B shows representative images of rat brain sections stained with an antibody against 8-hydroxy-2'-deoxyguanosine (a marker of oxidative damage to DNA). Nuclei are counterstained with DAPI. Magnification is 10× in top panels and 40× in bottom panels. NPLT was shown to greatly reduce oxidative in the cortex.

Figure 7A:
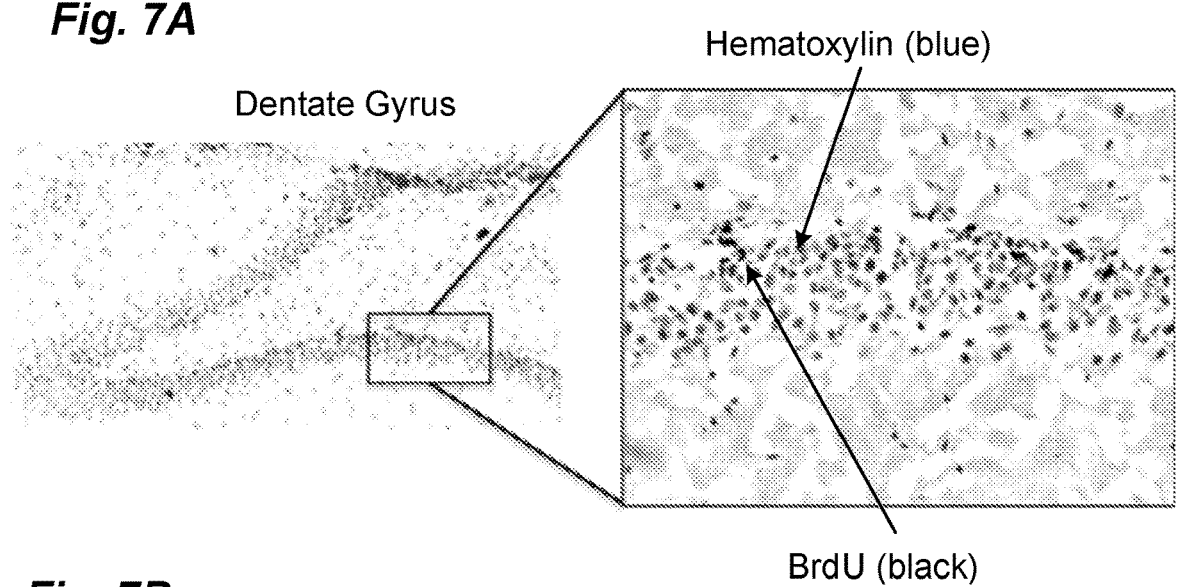
FIG. 7A shows representative images of the subgranular zone (SGZ) of the dentate gyrus of the hippocampus stained with an antibody against BrdU (shown in black). Hematoxylin was used to counterstain nuclei (shown in grey). Magnifications are 10× and 40× (insert).
Figure 7B:
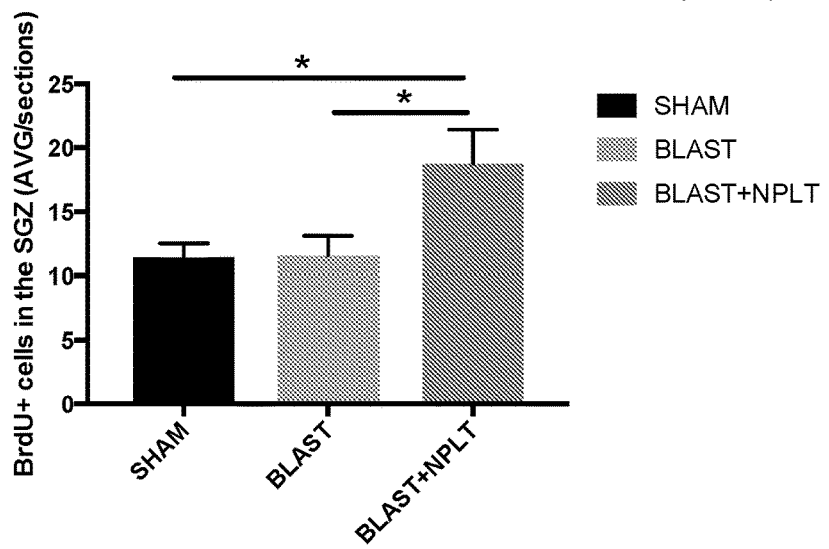
FIG. 7B shows quantification of the number of $BrdU^{pos}$ cells in the subgranular (SGZ) of the hippocampus dentate gyrus. Quantitative analysis of the number of $BrdU^{pos}$ cells in the SGZ on PID 10. *$P<0.05$; Two-way ANOVA followed by Tukey's multiple comparisons test. N=5 rats/group.
Figure 7C:
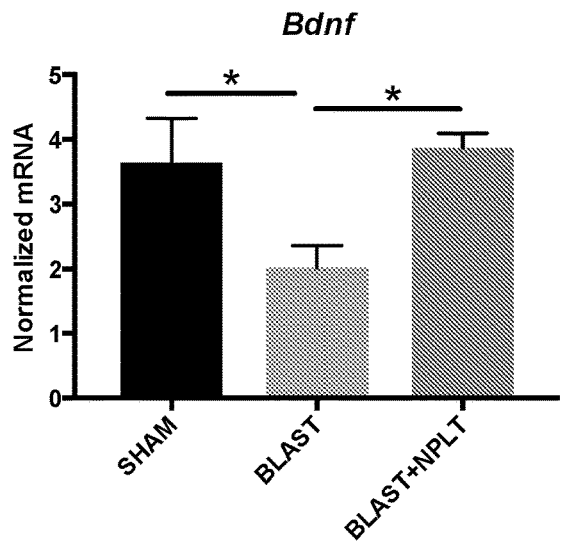
FIG. 7C shows quantification qRT-PCR analysis of BDNF mRNA expression in hippocampal neurons laser-captured on PID 7. Data was normalized to GAPDH expression and expressed as mean +/− SEM. N=4 for SHAM; N=3 for BLAST and BLAST+NPLT. * $P<0.05$ one-way ANOVA followed by Fisher's multiple comparisons test.

The neurotrophic factor BDNF plays a critical role in neuronal survival and also in supporting neurogenesis, a known mechanism by which new neurons are generated from neural stem cells in the subgranular zone of the hippocampal dentate gyrus throughout life. Levels of mRNA for BDNF were measured in the hippocampus seven days after blast or sham injury and it was found that while BDNF levels were significantly decreased after blast injury, NPLT prevented its decrease (FIG. 7C). Proliferation of progenitor cells in the dentate gyrus of the hippocampus was also measured using BrdU incorporation. FIG. 7A shows representative images of the dentate gyrus of the hippocampus stained with an antibody against BrdU (black staining). Nuclei are counterstained with Hematoxylin (blue staining). Magnification is 10×. The insert shows BrdU immunoreactivity at a higher magnification (40×). FIG. 7B shows quantification of the number of BrdU+ cells in the hippocampus dentate gyrus. It was found that 10 days after NPLT, a significantly higher number of BrdU$^{pos}$ cells are found in the subgranular zone of the dentate gyrus (FIG. 7B).

EXAMPLE 5 miRNA Expression

Figure 8A:
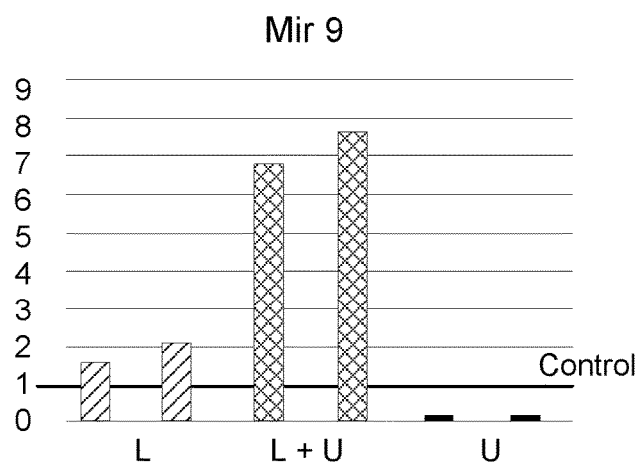
FIGS. 8A-8C show the expression of microRNAs known to regulate neurogenesis in neural stem cells (NCS) isolated from the hippocampus of adult rats and treated for 5 minutes with light alone (808 nm) in the first two bars of each chart, nano pulsed light (808 nm)+ultrasound in the third and fourth bars of each chart and ultrasound only (as generated by 808 nm pulsed light) in the fifth and sixths bars of each chart.
Figure 8B:
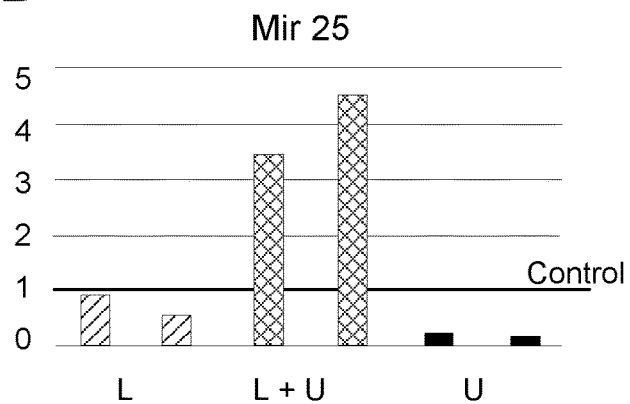
Figure 8C:
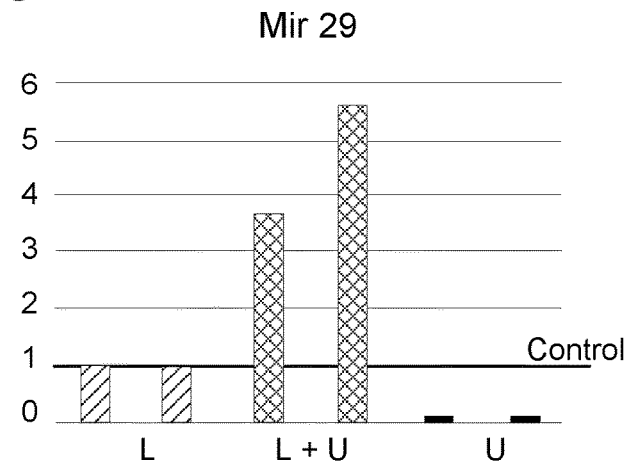

MicroRNAs (specifically miR9, miR29 and miR25) are known to regulate neurogenesis by regulating the differentiation of neural stem cells in the hippocampus (i.e. high levels of these miRNAs increase the generation of new neurons). Neural stem cells (NCS) were treated for 5 minutes with light alone (808 nm) in the first two bars of each chart, nano pulsed light (808 nm)+ultrasound in the third and fourth bars of each chart and ultrasound only (as generated by 808 nm pulsde light) in the fifth and sixths bars of each chart. FIG. 8A shows the expression of miR9. FIG. 8B shows the expression of miR29. FIG. 8C shows the expression of miR25. Only the combination of light and ultrasound (a unique property of our system) significantly increases the levels of these miRNAs in hippocampus neural stem cells (NSCs).

EXAMPLE 5

Longer Term Effects of NPLT

Figure 9:
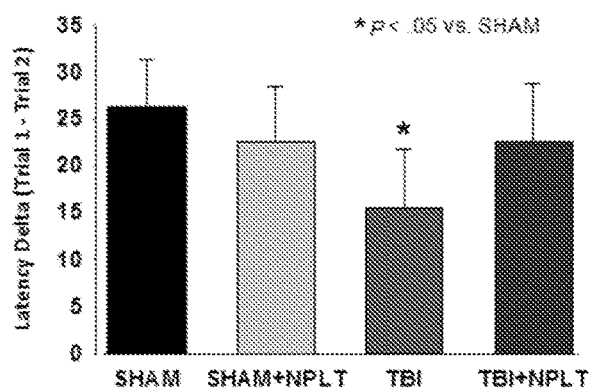
FIG. 9 shows the results of test of cognitive dysfunction in rats receiving fluid percussion injury (TBI) followed by either sham treatment or NPLT (TBI+NPLT). On days 11-15 post-injury the rats were tested using the Working Memory paradigm of the Morris Water Maze test. NPLT treatment prevented the impairment in working memory caused by TBI. N=14 rats/group

The continuing effects of NPLT was investigated by studies of TBI and TBI+NPLT groups up to two weeks after fluid percussive injury. FIG. 9 shows the results of test of cognitive dysfunction in rats receiving fluid percussion injury (TBI) followed by either sham treatment or NPLT (TBI+NPLT). On days 11-15 post-injury the rats were tested using the Working Memory paradigm of the Morris Water Maze test. NPLT treatment prevented the impairment in working memory caused by TBI.

Figure 10A:
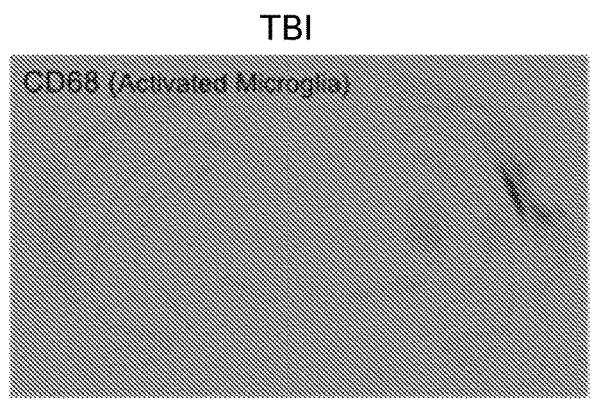
FIG. 10A-10D show representative coronal sections of rat brains immune-stained using selective antibodies against CD68 (a marker of activated microglia) and Iba1 (a general marker of all microglia). The rats received fluid percussion injury (TBI) followed by either sham treatment or NPLT (TBI+NPLT) 2 weeks prior to euthanasia.
Figure 10B:
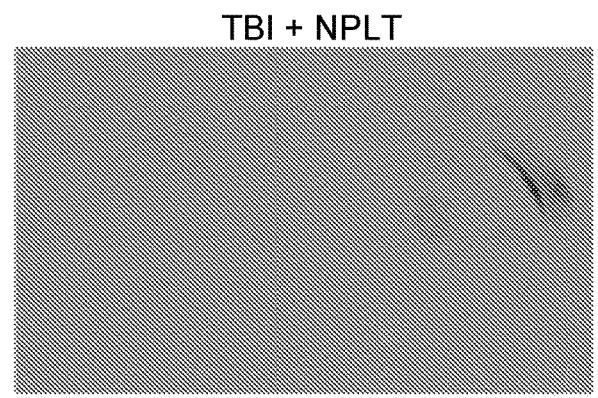
Figure 10C:
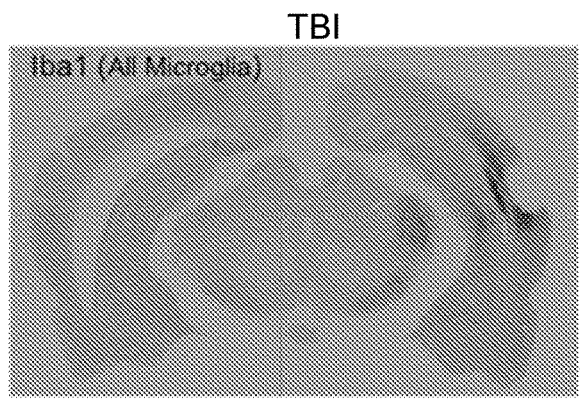
Figure 10D:
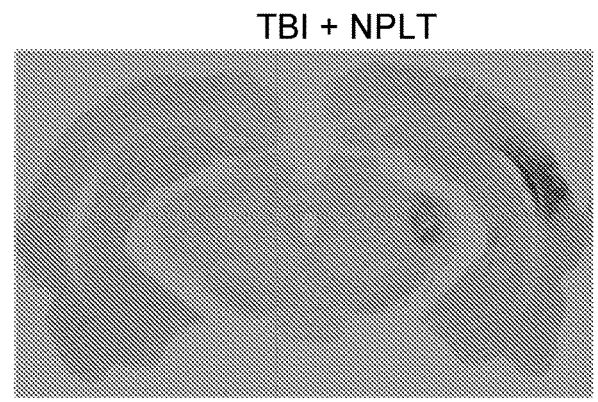

FIG. 10A-10D show representative coronal sections of rat brains immune-stained using selective antibodies against CD68 (a marker of activated microglia) and Iba1 (a general marker of all microglia). The rats received fluid percussion injury (TBI) followed by either sham treatment or NPLT (TBI+NPLT) 2 weeks prior to euthanasia. FIG. 10A represents coronal sections stained with anti-CD68 in TBI rats. FIG. 10B represents coronal sections stained with anti-CD68 in TBI +NPLT treated rats. FIG. 10C represents coronal sections stained with anti-Iba1 in TBI rats. FIG. 10D represents coronal sections stained with anti-Iba1 in TBI+NPLT treated rats.

EXAMPLE 6

Effects of NPLT on Deep Brain Structures

Figure 11A:
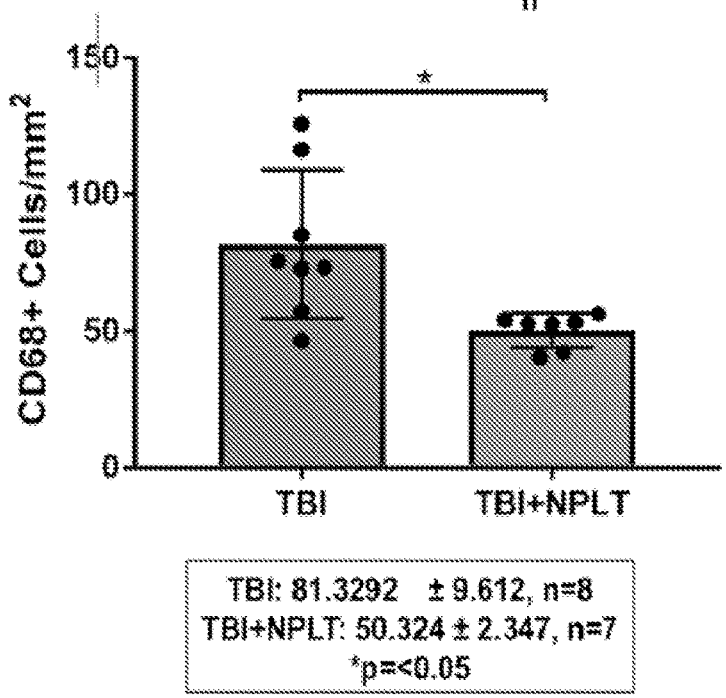
FIG. 11A compares the levels of CD68+ cells in the thalamus of rats with TBI and in TBI+NPLT treatment groups.
Figure 11B:
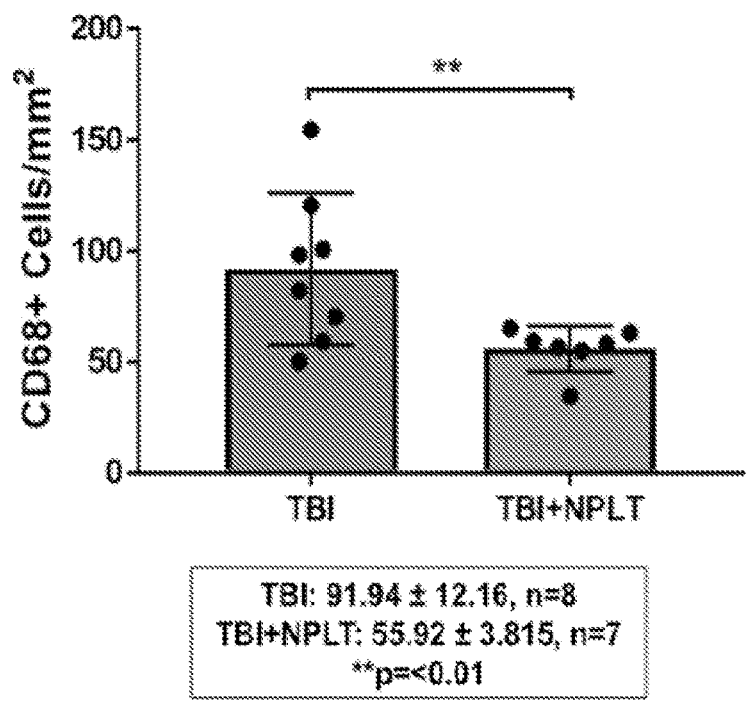
FIG. 11B compares the levels of CD68+ cells in the hippocampus of rats with TBI and in TBI+NPLT treatment groups.
Figure 11C:
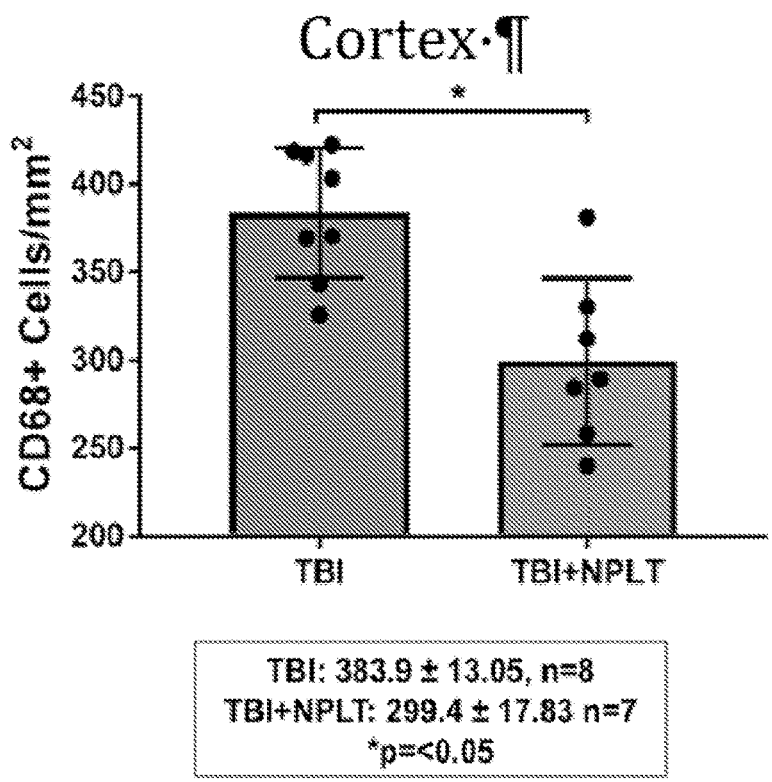
FIG. 11C compares the levels of CD68+ cells in the cortex of rats with TBI and in TBI+NPLT treatment groups.
Figure 11D:
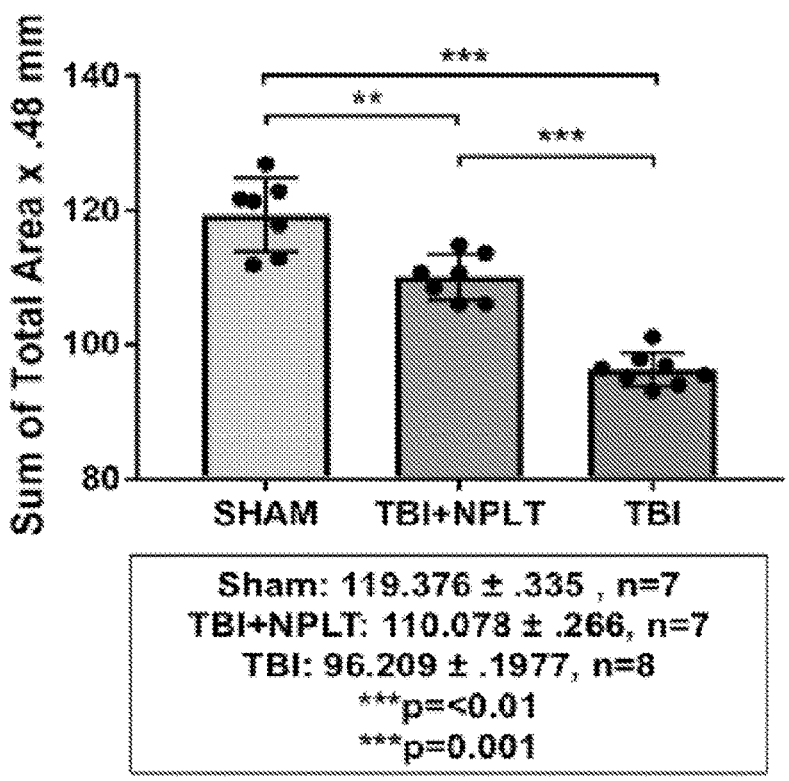
FIG. 11D compares the cortical volume in rats with TBI and in TBI+NPLT treatment groups.

The penetrating effects of NPLT was investigated by studies of TBI and TBI+NPLT groups in the thalamus, hippocampus and cortex of rats as well as investigating the value of NPLT is reductions of cortical volume due to trauma. FIG. 11A compares the levels of CD68+ cells in the thalamus of rats with TBI and in TBI+NPLT treatment groups FIG. 11B compares the levels of CD68+ cells in the hippocampus of rats with TBI and in TBI+NPLT treatment groups. FIG. 11C compares the levels of CD68+ cells in the cortex of rats with TBI and in TBI+NPLT treatment groups. FIG. 11D compares the cortical volume in rats with TBI and in TBI+NPLT treatment groups. NPLT resulted in significant reduction in inflammatory markers in the thalamus and hippocampus as well as the cortex and provided highly significant protection against loss of cortical volume.

EXAMPLE 7

Hemoglobin-Based NPLDT

NPLDT can be based on absorption of light by hemoglobin, which is a major tissue chromophore (absorber) in the near infra-red spectral range. Amplitude and frequency of optoacoustic waves generated in tissues by pulsed light in this spectral range are dependent on hemoglobin concentration/content in the tissue. Therefore, optoacoustics can provide diagnostic information before NPLT (baseline), during the NPLT, and after NPLT, if NPLT results in increase of blood flow and/or blood vessel dilatation in the treatment site/tissue that, in turn, increase hemoglobin concentration/content in the treatment site/tissue. Isosbestic wavelengths (which include 808 nm) can be used for the hemoglobin-based NPLDT. Methods for utilizing optoacoustics for hemoglobin monitoring can be found in "Continuous Optoacoustic Monitoring of Hemoglobin Concentration and Hematocrit." R. O. Esenaliev, M. Motamedi, D. S. Prough. (U.S. Pat. No. 6,751,490 and corresponding international patents, which are incorporated herein by reference in their entireties).

EXAMPLE 8

Oxygenation-Based NPLDT

NPLDT can be based on difference in light absorption between oxy- and deoxyhemoglobin in the near infra-red spectral range. Amplitude and frequency of optoacoustic waves generated in tissues by pulsed light in this spectral range are dependent on oxygenation in the tissue. Therefore, optoacoustics may provide diagnostic information before NPLT (baseline), during the NPLT, and after NPLT, if NPLT results in changes (for instance, increase) of blood oxygenation in the treatment site/tissue. A near infra-red spectral range from 680 nm to 1150 nm can be used the oxygenation-based NPLDT because oxy- and deoxyhemoglobin have different absorption in this spectral range. Methods for utilizing optoacoustics for oxygenation monitoring can be found in one or more of "Optoacoustic Monitoring of Blood Oxygenation." R. O. Esenaliev, M. Motamedi, D. S. Prough, A. A. Oraevsky. (U.S. Pat. No. 6,498,942); "System and Methods for Measuring Fetal Cerebral Oxygenation." R. O. Esenaliev, D. S. Prough, Y. Petrov, I. Petrov, G. Saade, G. Olson (U.S. Pat. No. 9,380,967); "Optoacoustic Monitoring of Multiple Parameters." D. S. Prough, R. O. Esenaliev, D. Deyo, Y. Petrov, I. Petrov. (Pending U.S. Patent Application Publication No. 2008/0255433A1); "Systems and Methods for Measuring Oxygenation." R. O. Esenaliev, D. S. Prough, Y. Petrov, I. Petrov, G. Saade, G. Olson (Pending U.S. Patent Application Publication No. 2016/0007892); and "Systems and Methods for Measuring Fetal Cerebral Oxygenation." R. O. Esenaliev, D. S. Prough, Y. Petrov, I. Petrov, G. Saade, G. Olson (Pending U.S. Patent Application Publication No. 2016/0007895); "Systems and Methods for Measuring Oxygenation." R. O. Esenaliev, D. S. Prough, Y. Petrov, I. Petrov, G. Saade, G. Olson, T. C. Cooper (Pending U.S. Patent Application Publication No. 2016/0015304) and "Systems and Methods for Measuring Neonatal Cerebral Oxygenation." R. O. Esenaliev, D. S. Prough, Y. Petrov, I. Petrov, C. J. Richardson (Pending U.S. Patent Application Publication No. 2016/0262674), each of which are incorporated by reference in their entireties.

EXAMPLE 9

Water-Based NPLDT

NPLDT can be based on absorption of light by water which is a major tissue chromophore (absorber) in the longer-wavelength part of the near infra-red spectral range (from 920 nm to 3000 nm). Optoacoustics can provide diagnostic information before NPLT (baseline), during the NPLT, and after NPLT, if NPLT results in increase of water content in the treatment site/tissue.

EXAMPLE 10

NPLDT Based on Different Chromophores

NPLDT can be based absorption of pulsed light by more than one chromophore. For instance, combination of the hemoglobin-, oxygenation-, and/or water-based NPLDT may provide more efficient therapy and more accurate diagnostics before, during, and after the therapy.

All publications, patents and patent applications cited herein are hereby incorporated by reference as if set forth in their entirety herein. While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

The invention claimed is:
1. A method for providing combined light and optoacoustic therapy to injured brain tissue, the method comprising:
applying a patient interface to a skin surface of a patient;
using the patient interface to deliver to the injured brain tissue therapeutic pulsed light having a pulse duration ranging from 1 femtosecond to 1 microsecond, a pulse energy of up to 15 mJ, a pulse repetition rate ranging from 0.1 Hz to 1 MHz, and a wavelength ranging from 680 to 950 nm; and
inducing therapeutic ultrasound waves within the injured brain tissue with the pulsed light, the ultrasound waves having a frequency of 0.01 to 100 MHz,
whereby the produced ultrasound waves and the pulsed light stimulate healing of the injured brain tissue,
wherein the injury of the injured brain tissue is selected from a traumatic brain injury, stroke, neurodegenerative disease, age-related (presenile) dementia, cognitive decline in the elderly as a consequence of atherosclerosis, and cognitive decline caused by normal pressure hydrocephalus.

2. The method of claim 1, wherein the pulsed light has a pulse duration ranging from about 1 femtosecond to about 10 nanoseconds.

3. The method of claim 2, wherein the pulsed light has a pulse duration ranging from about 1 nanosecond to about 10 nanoseconds.

4. The method of claim 1, further comprising using an optical absorber on the skin surface to increase an ultrasound wave dose induced in the injured brain tissue.

5. The method of claim 4, wherein the optical absorber is selected from the group consisting of liquid state absorbers, solid state absorbers, and gas state absorbers.

6. The method of claim 5, wherein the optical absorber is a liquid state absorber that includes strongly absorbing chromophores.

7. The method of claim 1, further comprising collecting from the pulsed light optoacoustic diagnostic information selected from one or more of tissue hemoglobin, oxygenation, and water content.

8. The method of claim 1, wherein the stimulated brain injured tissue is one or more of the thalamus, hippocampus, and cortex.

* * * * *